United States Patent
Kahook et al.

(10) Patent No.: US 11,076,948 B2
(45) Date of Patent: Aug. 3, 2021

(54) MODULAR INTRAOCULAR LENS DESIGNS, TOOLS AND METHODS

(71) Applicants: ClarVista Medical, Inc., Aliso Viejo, CA (US); The Regents of the University of Colorado, a body corporate, Denver, CO (US)

(72) Inventors: Malik Y. Kahook, Denver, CO (US); Glenn Sussman, Laguna Niguel, CA (US); Rudolph F. Zacher, Costa Mesa, CA (US); Paul J. McLean, North Oaks, MN (US); Harvey Uy, Quezon (PH); Robert Cionni, Salt Lake City, UT (US); Kerry Solomon, Sullivan's Island, SC (US)

(73) Assignees: Alcon Inc., Fribourg (CH); The Regents of the University of Colorado, a body corporate, Denver, CO (US)

( * ) Notice: Subject to any disclaimer, the term of this patent is extended or adjusted under 35 U.S.C. 154(b) by 12 days.

(21) Appl. No.: 16/017,295

(22) Filed: Jun. 25, 2018

(65) Prior Publication Data
US 2018/0368974 A1      Dec. 27, 2018

Related U.S. Application Data

(63) Continuation of application No. 15/342,806, filed on Nov. 3, 2016, now Pat. No. 10,028,824.
(Continued)

(51) Int. Cl.
*A61F 2/16* (2006.01)
*A61F 2/14* (2006.01)

(52) U.S. Cl.
CPC .......... *A61F 2/1648* (2013.01); *A61F 2/1662* (2013.01); *A61F 2/15* (2015.04);
(Continued)

(58) Field of Classification Search
CPC .............. A61F 2/1648; A61F 2002/169; A61F 2002/16902; A61F 2/1629; A61F 2/1651;
(Continued)

(56) References Cited

U.S. PATENT DOCUMENTS

| 3,937,222 A | 2/1976 | Banko |
| 4,092,743 A | 6/1978 | Kelman |

(Continued)

FOREIGN PATENT DOCUMENTS

| CA | 3 002 085 A1 | 5/2017 |
| EP | 0 478 929 A1 | 4/1992 |

(Continued)

OTHER PUBLICATIONS

PCT International Search Report and Written Opinion for International Application No. PCT/US2017/031066, dated Nov. 6, 2018 (9 pages).

(Continued)

*Primary Examiner* — Paul B Prebilic
(74) *Attorney, Agent, or Firm* — Bookoff McAndrews, PLLC

(57) ABSTRACT

Modular IOL systems including a base and a lens, wherein the lens includes tabs for connection to the base. The modular IOL allows for the lens to be adjusted or exchanged while leaving the base in place, either intra-operatively or post-operatively.

14 Claims, 17 Drawing Sheets

Related U.S. Application Data

(60) Provisional application No. 62/318,272, filed on Apr. 5, 2016, provisional application No. 62/256,579, filed on Nov. 17, 2015, provisional application No. 62/250,780, filed on Nov. 4, 2015.

(52) U.S. Cl.
CPC . *A61F 2002/169* (2015.04); *A61F 2002/1681* (2013.01); *A61F 2220/0033* (2013.01); *A61F 2250/006* (2013.01); *A61F 2250/0067* (2013.01)

(58) Field of Classification Search
CPC ...... A61F 2220/0033; A61F 2250/0008; A61F 2250/0053; A61F 2250/006; A61F 2250/0063; A61F 2250/0065; A61F 2250/0091
See application file for complete search history.

(56) References Cited

U.S. PATENT DOCUMENTS

| | | | |
|---|---|---|---|
| 4,168,547 | A | 9/1979 | Konstantinov et al. |
| 4,409,691 | A | 10/1983 | Levy |
| 4,435,856 | A | 3/1984 | L'Esperance |
| 4,681,102 | A | 7/1987 | Bartell |
| 4,693,245 | A | 9/1987 | Pao |
| 4,741,330 | A | 5/1988 | Hayhurst |
| 4,769,035 | A | 11/1988 | Kelman |
| 4,816,031 | A | 3/1989 | Pfoff |
| 4,828,558 | A | 5/1989 | Kelman |
| 4,842,601 | A | 6/1989 | Smith |
| 4,878,910 | A | 11/1989 | Koziol et al. |
| 4,911,715 | A | 3/1990 | Kelman |
| 4,932,971 | A | 6/1990 | Kelman |
| 4,950,272 | A | 8/1990 | Smirmaul |
| 4,960,418 | A | 10/1990 | Tennant |
| 5,026,396 | A | 6/1991 | Darin |
| 5,098,444 | A | 3/1992 | Feaster |
| 5,123,905 | A | 6/1992 | Kelman |
| 5,133,747 | A | 7/1992 | Feaster |
| 5,147,369 | A | 9/1992 | Wagner |
| 5,152,788 | A | 10/1992 | Isaacson et al. |
| 5,201,762 | A | 4/1993 | Hauber |
| 5,222,981 | A | 6/1993 | Werblin |
| 5,304,182 | A | 4/1994 | Rheinsish et al. |
| 5,354,335 | A | 10/1994 | Lipshitz et al. |
| 5,358,520 | A | 10/1994 | Patel |
| 5,366,502 | A | 11/1994 | Patel |
| 5,378,475 | A | 1/1995 | Smith et al. |
| 5,391,202 | A | 2/1995 | Lipshitz et al. |
| 5,395,378 | A | 3/1995 | McDonald |
| 5,410,375 | A | 4/1995 | Fiala |
| 5,417,369 | A | 5/1995 | Lipson |
| 5,507,805 | A | 4/1996 | Koeniger |
| 5,578,081 | A | 11/1996 | McDonald |
| 5,616,120 | A | 4/1997 | Andrew et al. |
| 5,628,795 | A | 5/1997 | Langerman |
| 5,628,798 | A | 5/1997 | Eggleston et al. |
| 5,728,155 | A | 3/1998 | Anello et al. |
| 5,769,890 | A | 6/1998 | McDonald |
| 5,814,103 | A | 9/1998 | Lipshitz et al. |
| 5,824,074 | A | 10/1998 | Koch |
| 5,860,985 | A | 1/1999 | Anschutz |
| 5,876,442 | A | 3/1999 | Lipshitz et al. |
| 5,895,422 | A | 4/1999 | Hauber |
| 5,902,598 | A | 5/1999 | Chen et al. |
| 5,928,283 | A | 7/1999 | Gross et al. |
| 5,944,725 | A | 8/1999 | Cicenas et al. |
| 5,964,802 | A | 10/1999 | Anello et al. |
| 5,968,094 | A | 10/1999 | Werblin et al. |
| 5,984,962 | A | 11/1999 | Anello et al. |
| 6,027,531 | A | 2/2000 | Tassignon |
| 6,066,171 | A | 5/2000 | Lipshitz et al. |
| 6,113,633 | A | 9/2000 | Portney |
| 6,136,026 | A | 10/2000 | Israel |
| 6,197,057 | B1 | 3/2001 | Peyman et al. |
| 6,197,058 | B1 | 3/2001 | Portney |
| 6,228,113 | B1 | 5/2001 | Kaufman |
| 6,231,603 | B1 | 5/2001 | Lang et al. |
| 6,277,146 | B1 | 8/2001 | Peyman et al. |
| 6,280,471 | B1 | 8/2001 | Peyman et al. |
| 6,358,280 | B1 | 3/2002 | Herrick |
| 6,413,276 | B1 | 7/2002 | Werblin |
| 6,423,094 | B1 | 7/2002 | Sarfarazi |
| 6,454,801 | B1 | 9/2002 | Portney |
| 6,464,725 | B2 | 10/2002 | Skotton |
| 6,488,708 | B2 | 12/2002 | Sarfarazi |
| 6,537,281 | B1 | 3/2003 | Portney |
| 6,551,354 | B1 | 4/2003 | Ghazizadeh et al. |
| 6,554,859 | B1 | 4/2003 | Lang et al. |
| 6,558,420 | B2 | 5/2003 | Green |
| 6,596,026 | B1 | 7/2003 | Gross et al. |
| 6,599,317 | B1 | 7/2003 | Weinschenk, III et al. |
| 6,616,692 | B1 | 9/2003 | Glick et al. |
| 6,638,304 | B2 | 10/2003 | Azar |
| 6,685,741 | B2 | 2/2004 | Landreville et al. |
| 6,695,881 | B2 | 2/2004 | Peng et al. |
| 6,764,511 | B2 | 7/2004 | Zadno-Azizi et al. |
| 6,767,363 | B1 | 7/2004 | Bandhauer et al. |
| 6,786,934 | B2 | 9/2004 | Zadno-Azizi et al. |
| 6,797,004 | B1 | 9/2004 | Brady et al. |
| 6,818,017 | B1 | 11/2004 | Shu |
| 6,846,326 | B2 | 1/2005 | Zadno-Azizi et al. |
| 6,858,040 | B2 | 2/2005 | Nguyen et al. |
| 6,899,732 | B2 | 5/2005 | Zadno-Azizi et al. |
| 6,926,736 | B2 | 8/2005 | Peng et al. |
| 6,960,231 | B2 | 11/2005 | Tran |
| 6,969,403 | B2 | 11/2005 | Peng et al. |
| 6,972,032 | B2 | 12/2005 | Aharoni et al. |
| 6,972,034 | B2 | 12/2005 | Tran et al. |
| 6,991,651 | B2 | 1/2006 | Portney |
| 7,008,447 | B2 | 3/2006 | Koziol |
| 7,041,134 | B2 | 5/2006 | Nguyen et al. |
| 7,081,134 | B2 | 7/2006 | Cukrowski |
| 7,087,080 | B2 | 8/2006 | Zadno-Azizi et al. |
| 7,097,660 | B2 | 8/2006 | Portney |
| 7,101,397 | B2 | 9/2006 | Aharoni |
| 7,118,596 | B2 | 10/2006 | Zadno-Azizi et al. |
| 7,122,053 | B2 | 10/2006 | Esch |
| 7,125,422 | B2 | 10/2006 | Woods et al. |
| 7,186,266 | B2 | 3/2007 | Peyman |
| 7,198,640 | B2 | 4/2007 | Nguyen |
| 7,220,278 | B2 | 5/2007 | Peyman |
| 7,223,288 | B2 | 5/2007 | Zhang et al. |
| 7,226,478 | B2 | 6/2007 | Ting et al. |
| 7,238,201 | B2 | 7/2007 | Portney et al. |
| 7,300,464 | B2 | 11/2007 | Tran |
| 7,316,713 | B2 | 1/2008 | Zhang |
| 7,452,378 | B2 | 11/2008 | Zadno-Azizi et al. |
| 7,582,113 | B2 | 9/2009 | Terwee |
| 7,591,849 | B2 | 9/2009 | Richardson |
| 7,645,299 | B2 | 1/2010 | Koziol |
| 7,662,179 | B2 | 2/2010 | Sarfarazi |
| 7,727,277 | B2 | 6/2010 | Aharoni et al. |
| 7,736,390 | B2 | 6/2010 | Aharoni et al. |
| 7,780,729 | B2 | 8/2010 | Nguyen et al. |
| 7,811,320 | B2 | 10/2010 | Werblin |
| 7,857,850 | B2 | 12/2010 | Mentak et al. |
| 7,871,437 | B2 | 1/2011 | Hermans et al. |
| 7,918,886 | B2 | 4/2011 | Aharoni et al. |
| 7,985,253 | B2 | 7/2011 | Cumming |
| 7,993,399 | B2 | 8/2011 | Peyman |
| 7,998,198 | B2 | 8/2011 | Angelopoulos et al. |
| 8,012,204 | B2 | 9/2011 | Weinschenk, III et al. |
| 8,034,106 | B2 | 10/2011 | Mentak et al. |
| 8,034,107 | B2 | 10/2011 | Stenger |
| 8,034,108 | B2 | 10/2011 | Bumbalough |
| 8,062,361 | B2 | 11/2011 | Nguyen et al. |
| 8,066,768 | B2 | 11/2011 | Werblin |
| 8,066,769 | B2 | 11/2011 | Werblin |
| 8,128,693 | B2 | 3/2012 | Tran et al. |
| 8,137,399 | B2 | 3/2012 | Glazier et al. |

(56) References Cited

U.S. PATENT DOCUMENTS

| | | | |
|---|---|---|---|
| 8,167,941 B2 | 5/2012 | Boyd et al. |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,273,123 B2 | 9/2012 | Ben Nun |
| 8,287,593 B2 | 10/2012 | Portney |
| 8,377,124 B2 | 2/2013 | Hong et al. |
| 8,425,597 B2 | 4/2013 | Glick et al. |
| 8,486,142 B2 | 7/2013 | Bumbalough |
| 8,551,167 B2 | 10/2013 | Cuevas |
| 8,579,972 B2 | 11/2013 | Rombach |
| 8,663,235 B2 | 3/2014 | Tassignon |
| 8,728,158 B2 | 5/2014 | Whitsett |
| 8,758,434 B2 | 6/2014 | Scott |
| 8,900,300 B1 | 12/2014 | Wortz |
| 9,011,532 B2 | 4/2015 | Bumbalough |
| 9,095,424 B2 | 8/2015 | Kahook et al. |
| 9,125,736 B2 | 9/2015 | Kahook |
| 9,186,244 B2 | 11/2015 | Silvestrini et al. |
| 9,198,752 B2 | 12/2015 | Woods |
| 9,220,590 B2 | 12/2015 | Beer |
| 9,289,287 B2 | 3/2016 | Kahook |
| 9,364,316 B1 | 6/2016 | Kahook |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,681,946 B2 | 6/2017 | Kahook et al. |
| 9,877,825 B2 | 1/2018 | Kahook et al. |
| 9,925,040 B2 | 3/2018 | Kahook et al. |
| 10,004,596 B2 | 6/2018 | Brady et al. |
| 10,028,824 B2 | 7/2018 | Kahook et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 2002/0138140 A1 | 9/2002 | Hanna |
| 2003/0088253 A1 | 5/2003 | Seil |
| 2003/0144733 A1 | 7/2003 | Brady et al. |
| 2003/0158560 A1 | 8/2003 | Portney |
| 2004/0010310 A1 | 1/2004 | Peymen |
| 2004/0106993 A1 | 6/2004 | Portney |
| 2004/0148022 A1 | 7/2004 | Eggleston |
| 2004/0236422 A1 | 11/2004 | Zhang et al. |
| 2004/0243142 A1 | 12/2004 | Siepser |
| 2005/0015144 A1 | 1/2005 | Tran |
| 2005/0021139 A1 | 1/2005 | Shadduck |
| 2005/0027354 A1 | 2/2005 | Brady et al. |
| 2005/0187621 A1 | 5/2005 | Brady |
| 2005/0125058 A1 | 6/2005 | Cumming et al. |
| 2005/0131535 A1 | 6/2005 | Woods |
| 2005/0273163 A1 | 12/2005 | Tran et al. |
| 2006/0111776 A1 | 5/2006 | Glick et al. |
| 2006/0253196 A1 | 11/2006 | Woods |
| 2006/0286147 A1 | 12/2006 | Salamone et al. |
| 2007/0123981 A1 | 5/2007 | Tassignon |
| 2008/0046077 A1 | 2/2008 | Cumming |
| 2008/0103592 A1 | 5/2008 | Maloney |
| 2008/0183289 A1 | 7/2008 | Werblin |
| 2008/0215147 A1 | 9/2008 | Werblin |
| 2009/0005864 A1 | 1/2009 | Eggleston |
| 2010/0016964 A1 | 1/2010 | Werblin |
| 2010/0204787 A1 | 8/2010 | Noy |
| 2010/0298933 A1 | 11/2010 | Knox et al. |
| 2011/0040378 A1 | 2/2011 | Werblin |
| 2011/0054600 A1 | 3/2011 | Bumbalough |
| 2011/0251686 A1 | 10/2011 | Masket |
| 2011/0257742 A1 | 10/2011 | Bumbalough |
| 2011/0307058 A1 | 12/2011 | Beer |
| 2011/0313521 A1 | 12/2011 | Angelopoulos |
| 2012/0078364 A1 | 3/2012 | Stenger |
| 2012/0179249 A1 | 7/2012 | Coleman |
| 2012/0209305 A1 | 8/2012 | Deodhar et al. |
| 2013/0053954 A1 | 2/2013 | Rao et al. |
| 2013/0066422 A1 | 3/2013 | Dworschak et al. |
| 2013/0184815 A1 | 7/2013 | Roholt |
| 2013/0190868 A1 | 7/2013 | Kahook et al. |
| 2013/0296694 A1 | 11/2013 | Ehlers et al. |
| 2013/0304204 A1 | 11/2013 | Bumbalough |
| 2013/0310931 A1 | 11/2013 | Kahook et al. |
| 2014/0052246 A1* | 2/2014 | Kahook ............... A61F 9/007 623/6.41 |
| 2014/0081178 A1 | 3/2014 | Pletcher et al. |
| 2014/0084489 A1 | 3/2014 | Etzkorn |
| 2014/0085599 A1 | 3/2014 | Etzkorn |
| 2014/0085600 A1 | 3/2014 | Pletcher et al. |
| 2014/0085602 A1 | 3/2014 | Ho et al. |
| 2014/0087452 A1 | 3/2014 | Liu et al. |
| 2014/0088381 A1 | 3/2014 | Etzkorn et al. |
| 2014/0098226 A1 | 4/2014 | Pletcher et al. |
| 2014/0180403 A1 | 6/2014 | Silvestrini et al. |
| 2014/0180411 A1 | 6/2014 | Tornambe et al. |
| 2014/0192311 A1 | 7/2014 | Pletcher et al. |
| 2014/0194710 A1 | 7/2014 | Ho et al. |
| 2014/0194713 A1 | 7/2014 | Liu |
| 2014/0194773 A1 | 7/2014 | Pletcher et al. |
| 2014/0371852 A1 | 12/2014 | Aharoni et al. |
| 2015/0105760 A1 | 4/2015 | Rao et al. |
| 2015/0157452 A1 | 6/2015 | Maliarov |
| 2015/0230981 A1 | 8/2015 | Kahook et al. |
| 2016/0030161 A1 | 2/2016 | Brady et al. |
| 2016/0074154 A1 | 3/2016 | Woods |
| 2016/0128826 A1 | 5/2016 | Silvestrini et al. |
| 2016/0157995 A1 | 6/2016 | Beer |
| 2016/0184089 A1 | 6/2016 | Dudee et al. |
| 2016/0199176 A1 | 7/2016 | Wanders |
| 2016/0235524 A1 | 8/2016 | Wortz et al. |
| 2016/0235587 A1 | 8/2016 | Kahook et al. |
| 2016/0250020 A1 | 9/2016 | Kahook et al. |
| 2016/0310264 A1 | 10/2016 | Akura |
| 2016/0317286 A1 | 11/2016 | Brady et al. |
| 2016/0317287 A1 | 11/2016 | Silvestrini et al. |
| 2016/0331519 A1 | 11/2016 | Kahook et al. |
| 2016/0338825 A1 | 11/2016 | Wortz et al. |
| 2017/0119521 A1 | 5/2017 | Kahook et al. |
| 2017/0319332 A1 | 11/2017 | Kahook et al. |
| 2018/0014928 A1 | 1/2018 | Kahook et al. |
| 2018/0161153 A1 | 6/2018 | Kahook et al. |
| 2018/0177639 A1 | 6/2018 | Rao et al. |
| 2018/0344453 A1 | 12/2018 | Brady et al. |
| 2019/0000612 A1 | 1/2019 | Rao et al. |
| 2019/0021848 A1 | 1/2019 | Kahook et al. |
| 2019/0099263 A1 | 4/2019 | Brady et al. |

FOREIGN PATENT DOCUMENTS

| | | |
|---|---|---|
| EP | 1 138 282 A1 | 10/2001 |
| EP | 1 457 170 A1 | 9/2004 |
| EP | 1 743 601 A1 | 1/2007 |
| EP | 1 862 147 A1 | 12/2007 |
| EP | 2 042 124 A1 | 4/2009 |
| EP | 1 296 616 B1 | 5/2012 |
| EP | 1 871 299 B1 | 8/2012 |
| JP | 62-022641 | 1/1987 |
| JP | 01-097450 | 4/1989 |
| JP | 04-505715 | 10/1992 |
| JP | 06-165793 | 6/1994 |
| JP | 06-189985 | 7/1994 |
| JP | 63-089154 | 4/1998 |
| JP | 2003-505197 | 2/2003 |
| JP | 2003-524503 | 8/2003 |
| JP | 2007-512907 | 5/2007 |
| JP | 2008-525156 | 7/2008 |
| JP | 2008-532617 | 8/2008 |
| JP | 2010-516394 | 5/2010 |
| JP | 2012-040326 | 3/2012 |
| JP | 2013-512033 | 4/2013 |
| JP | 5705529 B2 | 4/2015 |
| RU | 2026652 C1 | 1/1995 |
| WO | WO 94/28825 A1 | 12/1994 |
| WO | WO 03/039335 A2 | 5/2003 |
| WO | WO 2006/103674 A2 | 10/2006 |

(56) References Cited

FOREIGN PATENT DOCUMENTS

| WO | WO 2006/118452 A1 | 11/2006 | | |
|----|-------------------|---------|---|---|
| WO | WO 2008/094518 A1 | 8/2008  | | |
| WO | WO 2010/002215 A2 | 1/2010  | | |
| WO | WO 2012/023133 A1 | 2/2012  | | |
| WO | WO 2012/071146 A2 | 5/2012  | | |
| WO | WO 2013/112589 A1 | 8/2013  | | |
| WO | WO 2013/158942 A1 | 10/2013 | | |
| WO | WO 2014/197170 A1 | 12/2014 | | |
| WO | WO 2014/204575 A1 | 12/2014 | | |
| WO | WO-2014197170 A1 * | 12/2014 | ........... | A61F 2/1648 |
| WO | WO 2016/022995 A2 | 2/2016  | | |
| WO | WO 2016/130209 A1 | 8/2016  | | |

OTHER PUBLICATIONS

PCT International Search Report and Written Opinion for International Application No. PCT/US2013/022752, dated Apr. 19, 2013 (12 pages).

PCT International Search Report and Written Opinion for International Application No. PCT/US2014/037646, dated Aug. 18, 2014 (14 pages).

PCT International Search Report and Written Opinion for International Application No. PCT/US2015/014046, dated Apr. 9, 2015 (14 pages).

PCT International Search Report and Written Opinion for International Application No. PCT/US2015/067035, dated Apr. 12, 2016 (17 pages).

PCT International Search Report and Written Opinion for International Application No. PCT/US2016/060350, dated Jan. 27, 2017 (14 pages).

* cited by examiner

MODULAR INTRAOCULAR LENS DESIGNS, TOOLS AND METHODS

CROSS-REFERENCE TO RELATED APPLICATIONS

This application is a continuation of U.S. application Ser. No. 15/342,806, filed Nov. 3, 2016, now U.S. Pat. No. 10,028,824 which claims the benefits under 35 U.S.C. § 119(e) of priority to U.S. Provisional Patent Application No. 62/318,272, filed Apr. 5, 2016, entitled "MODULAR INTRAOCULAR LENS DESIGNS, TOOLS AND METHODS," U.S. Provisional Patent Application No. 62/256,579, filed Nov. 17, 2015, entitled "MODULAR INTRAOCULAR LENS DESIGNS, TOOLS AND METHODS," and U.S. Provisional Patent Application No. 62/250,780, filed Nov. 4, 2015, entitled "MODULAR INTRAOCULAR LENS DESIGNS, TOOLS AND METHODS," each of which is incorporated herein by reference. This application is related to U.S. patent application Ser. No. 15/890,914, filed Mar. 19, 2018, entitled "MODULAR INTRAOCULAR LENS DESIGNS, TOOLS AND METHODS, which is related to U.S. patent application Ser. No. 15/218,658, filed Jul. 25, 2016, entitled "MODULAR INTRAOCULAR LENS DESIGNS, TOOLS AND METHODS," now U.S. Pat. No. 9,925,040, which is related to U.S. patent application Ser. No. 15/150,360, entitled "MODULAR INTRAOCULAR LENS DESIGNS, TOOLS AND METHODS," now U.S. Pat. No. 9,421,088, which is related to U.S. patent application Ser. No. 14/828,083, filed Aug. 17, 2015, entitled "MODULAR INTRAOCULAR LENS DESIGNS, TOOLS AND METHODS," now U.S. Pat. No. 9,364,316, which claims the benefits under 35 U.S.C. § 119(e) of priority to U.S. Provisional Patent Application No. 62/110,241, filed Jan. 30, 2015, entitled "MODULAR INTRAOCULAR LENS DESIGNS, TOOLS AND METHODS," each of which is incorporated herein by reference. This application also is related to U.S. patent application Ser. No. 14/610,360, filed Jan. 30, 2015, entitled "MODULAR INTRAOCULAR LENS DESIGNS, TOOLS AND METHODS," which claims the benefits under 35 U.S.C. § 119(e) of priority to U.S. Provisional Patent Application No. 61/941,167, filed Feb. 18, 2014, entitled "MODULAR INTRAOCULAR LENS DESIGNS, TOOLS AND METHODS," each of which is incorporated herein by reference. This application also is related to U.S. patent application Ser. No. 15/054,915, filed Feb. 26, 2016, entitled "MODULAR INTRAOCULAR LENS DESIGNS & METHODS," which is related to U.S. patent application Ser. No. 13/969,115, filed Aug. 16, 2013, entitled "MODULAR INTRAOCULAR LENS DESIGNS & METHODS," now U.S. Pat. No. 9,289,287, which claims the benefits under 35 U.S.C. § 119(e) of priority to U.S. Provisional Patent Application No. 61/830,491, filed Jun. 3, 2013, entitled "MODULAR INTRAOCULAR LENS DESIGNS AND METHODS," each of which is incorporated herein by reference. This application also is related to U.S. patent application Ser. No. 15/176,582, filed Jul. 8, 2016, entitled "MODULAR INTRAOCULAR LENS DESIGNS AND METHODS," now U.S. Pat. No. 9,877,825, which is related to U.S. patent application Ser. No. 14/808,022, filed Jul. 24, 2015, entitled "MODULAR INTRAOCULAR LENS DESIGNS AND METHODS," now U.S. Pat. No. 9,387,069, which is related to U.S. patent application Ser. No. 13/937,761, filed Jul. 9, 2013, entitled "MODULAR INTRAOCULAR LENS DESIGNS AND METHODS," now U.S. Pat. No. 9,125,736, which is related to U.S. patent application Ser. No. 13/748,207, filed Jan. 23, 2013, entitled "MODULAR INTRAOCULAR LENS DESIGNS & METHODS," now U.S. Pat. No. 9,095,424, which claims the benefits under 35 U.S.C. § 119(e) of priority of U.S. Provisional Patent Application No. 61/589,981, filed on Jan. 24, 2012, entitled "LASER ETCHING OF IN SITU INTRAOCULAR LENS AND SUCCESSIVE SECONDARY LENS IMPLANTATION," and of U.S. Provisional Patent Application No. 61/677,213, filed on Jul. 30, 2012, entitled "MODULAR INTRAOCULAR LENS DESIGNS & METHODS," each of which is incorporated herein by reference.

TECHNICAL FIELD

The present disclosure generally relates to intraocular lenses (IOLs). More specifically, the present disclosure relates to embodiments of modular IOL designs, methods and associated tools.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent (e.g., cloudy), vision deteriorates because of the diminished light, which can be transmitted to the retina. This deficiency in the lens of the eye is medically known as a cataract. An accepted treatment for this condition is surgical removal of the lens from the capsular bag and placement of an artificial intraocular lens (IOL) in the capsular bag. In the United States, the majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The diseased lens, once removed, is replaced by an IOL.

After cataract surgery to implant an IOL, the optical result may be suboptimal or may need adjustment over time. For example, shortly after the procedure, it may be determined that the refractive correction is erroneous leading to what is sometimes called "refractive surprise." Also for example, long after the procedure, it may be determined that the patient needs or desires a different correction, such as a stronger refractive correction, an astigmatism correction, or a multifocal correction.

In each of these cases, a surgeon may be reluctant to attempt removal of the suboptimal IOL from the capsular bag and replacement with a new IOL. In general, manipulation of the capsular bag to remove an IOL risks damage to the capsular bag including posterior rupture. This risk increases over time as the capsular bag collapses around the IOL and tissue ingrowth surrounds the haptics of the IOL. Thus, it would be desirable to be able to correct or modify the optical result without the need to remove the IOL or manipulate the capsular bag.

Thus, there remains a need for an IOL system and method that allows for correction or modification of the optical result using a lens that can be attached to a base or primary lens without the need to manipulate the capsular bag.

SUMMARY OF THE DISCLOSURE

Embodiments of the present disclosure provide a modular IOL system including intraocular base and optic components, which, when combined, form a modular IOL. In general, the modular IOL allows for the lens to be adjusted or exchanged while leaving the base in place, either intra-operatively or post-operatively.

In one embodiment, a modular IOL system includes an annular base having two radially outward extending haptics. The base defines a center hole and an inside perimeter, with a radially inward open recess around the inside perimeter. The modular IOL system also includes a lens having an optical body with first and second tabs extending radially outward from the optical body. The base and lens may be assembled with the first and second tabs of the lens disposed in the recess of the base. The first tab may be an actuatable spring, and the second tab may be a non-actuatable extension. The first tab may require radial compression for assembly of the lens with the base. The first tab may comprise a pair of cantilever springs, each with one end attached the optical body and one end free.

Various techniques are also disclosed to deliver and/or assemble modular IOL systems. These techniques may be applied to modular IOL embodiments not specifically described herein.

The modular IOL systems, tools and methods according to embodiments of the present disclosure may be applied to a variety of IOL types, including fixed monofocal, multifocal, toric, accommodative, and combinations thereof. In addition, the modular IOL systems, tools and methods according to embodiments of the present disclosure may be used to treat, for example: cataracts, large optical errors in myopic (near-sighted), hyperopic (far-sighted), and astigmatic eyes, ectopia lentis, aphakia, pseudophakia, and nuclear sclerosis.

Various other aspects of embodiments of the present disclosure are described in the following detailed description and drawings.

BRIEF DESCRIPTION OF THE DRAWINGS

The drawings illustrate example embodiments of the present disclosure. The drawings are not necessarily to scale, may include similar elements that are numbered the same, and may include dimensions (in millimeters) and angles (in degrees) by way of example, not necessarily limitation. In the drawings.

DETAILED DESCRIPTION

Figure 1:
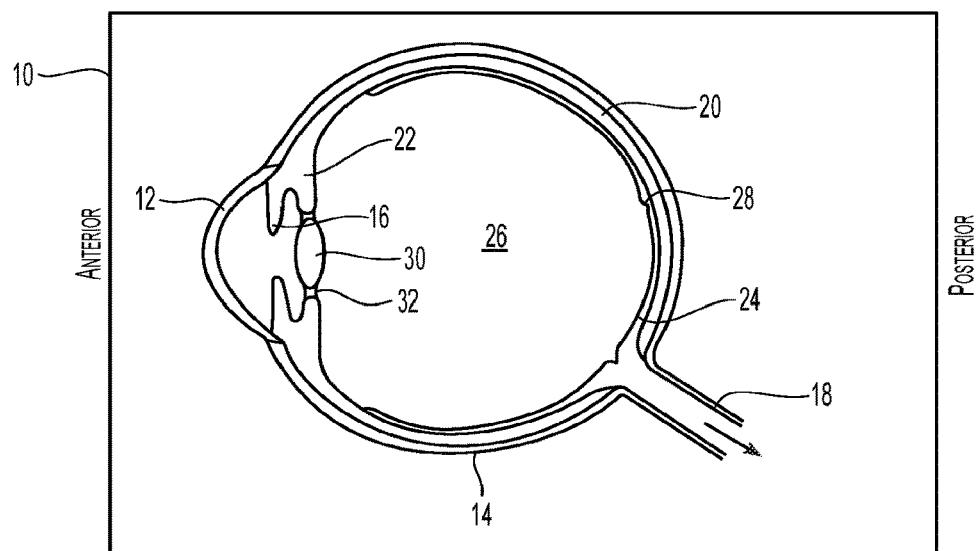
FIG. 1 is a schematic diagram of the human eye shown in cross section.

With reference to FIG. 1, the human eye 10 is shown in cross section. The eye 10 has been described as an organ that reacts to light for several purposes. As a conscious sense organ, the eye allows vision. Rod and cone cells in the retina 24 allow conscious light perception and vision including color differentiation and the perception of depth. In addition, the human eye's non-image-forming photosensitive ganglion cells in the retina 24 receive light signals which affect adjustment of the size of the pupil, regulation and suppression of the hormone melatonin, and entrainment of the body clock.

The eye 10 is not properly a sphere; rather it is a fused two-piece unit. The smaller frontal unit, more curved, called the cornea 12 is linked to the larger unit called the sclera 14. The corneal segment 12 is typically about 8 mm (0.3 in) in radius. The sclera 14 constitutes the remaining five-sixths; its radius is typically about 12 mm. The cornea 12 and sclera 14 are connected by a ring called the limbus. The iris 16, the color of the eye, and its black center, the pupil, are seen instead of the cornea 12 due to the cornea's 12 transparency. To see inside the eye 10, an ophthalmoscope is needed, since light is not reflected out. The fundus (area opposite the pupil), which includes the macula 28, shows the characteristic pale optic disk (papilla), where vessels entering the eye pass across and optic nerve fibers 18 depart the globe.

Thus, the eye 10 is made up of three coats, enclosing three transparent structures. The outermost layer is composed of the cornea 12 and sclera 14. The middle layer consists of the choroid 20, ciliary body 22, and iris 16. The innermost layer is the retina 24, which gets its circulation from the vessels of the choroid 20 as well as the retinal vessels, which can be seen within an ophthalmoscope. Within these coats are the aqueous humor, the vitreous body 26, and the flexible lens 30. The aqueous humor is a clear fluid that is contained in two areas: the anterior chamber between the cornea 12 and the iris 16 and the exposed area of the lens 30; and the posterior chamber, between the iris 16 and the lens 30. The lens 30 is suspended to the ciliary body 22 by the suspensory ciliary ligament 32 (Zonule of Zinn), made up of fine transparent fibers. The vitreous body 26 is a clear jelly that is much larger than the aqueous humor.

The crystalline lens 30 is a transparent, biconvex structure in the eye that, along with the cornea 12, helps to refract light to be focused on the retina 24. The lens 30, by changing its shape, functions to change the focal distance of the eye so that it can focus on objects at various distances, thus allowing a sharp real image of the object of interest to be formed on the retina 24. This adjustment of the lens 30 is known as accommodation, and is similar to the focusing of a photographic camera via movement of its lenses.

The lens has three main parts: the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are found predominantly on the anterior side of the lens but extend posteriorly just beyond the equator.

The lens capsule is a smooth, transparent basement membrane that completely surrounds the lens. The capsule is elastic and is composed of collagen. It is synthesized by the lens epithelium and its main components are Type IV collagen and sulfated glycosaminoglycans (GAGs). The capsule is very elastic and so causes the lens to assume a more globular shape when not under the tension of the zonular fibers, which connect the lens capsule to the ciliary body 22. The capsule varies between approximately 2-28 micrometers in thickness, being thickest near the equator and thinnest near the posterior pole. The lens capsule may be involved with the higher anterior curvature than posterior of the lens.

Various diseases and disorders of the lens 30 may be treated with an IOL. By way of example, not necessarily limitation, a modular IOL according to embodiments of the present disclosure may be used to treat cataracts, large optical errors in myopic (near-sighted), hyperopic (farsighted), and astigmatic eyes, ectopia lentis, aphakia, pseudophakia, and nuclear sclerosis. However, for purposes of description, the modular IOL embodiments of the present disclosure are described with reference to cataracts.

The following detailed description describes various embodiments of a modular IOL system including primary and secondary intraocular components, namely an intraocular base configured to releasably receive an intraocular optic. Features described with reference to any one embodiment may be applied to and incorporated into other embodiments.

Figure 2:
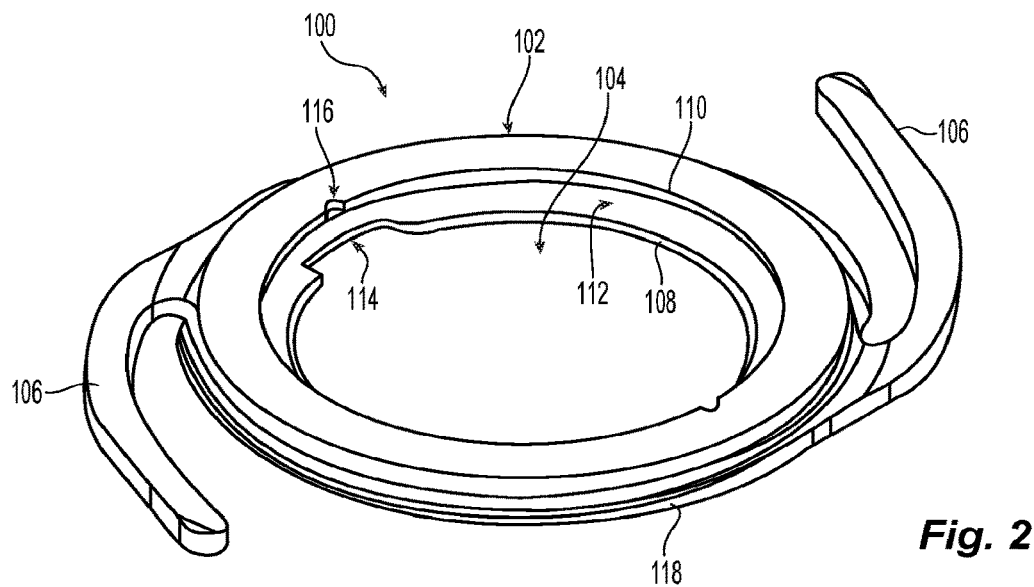
FIG. 2 is a perspective view of a base of a modular IOL according to the present disclosure.
Figure 3:
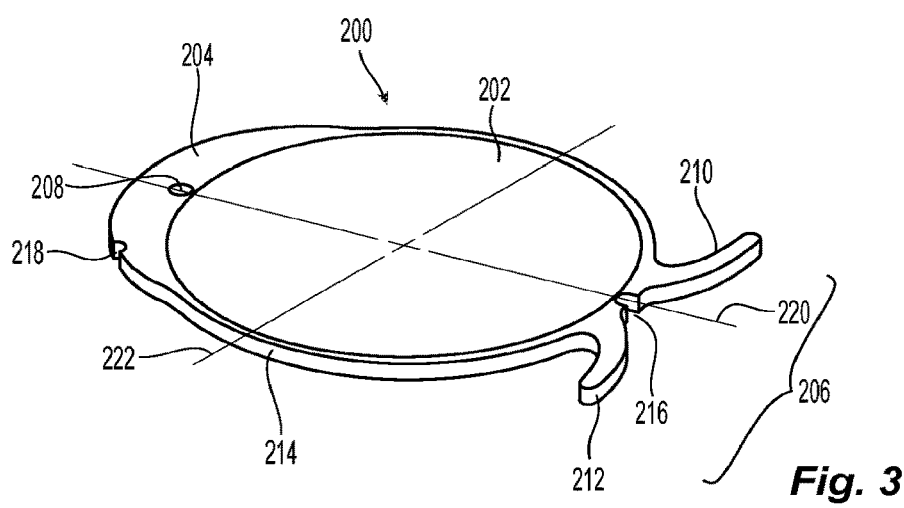
FIG. 3 is a perspective view of a lens of a modular IOL according to the present disclosure.

With reference to FIGS. 2 and 3 a base 100 and a lens 200 form an embodiment of a modular IOL when assembled. A general description of the base 100 and lens follows, with further detailed provided in U.S. patent application Ser. No. 14/828,083, which is hereby fully incorporated by reference.

With specific reference to FIG. 2, the base 100 portion of the modular IOL includes an annular ring 102 defining a center hole 104. A pair of haptics 106 extend radially outward from the annular ring 102. The annular ring 102 includes a lower rim 108, an upper rim 110 and an inward-facing lateral wall to define an inward-facing recess 112, into which the lens 200 may be inserted to form a modular IOL.

The lower rim 108 of the base 100 may include one or more vent cutouts 114, which aid in removing visco-elastic intra-operatively. The upper rim 110 may include one or more notches 116 to provide access for a probe (e.g., Sinskey hook) intra-operatively, which allows the base 100 to be more easily manipulated. The base 100 may include an outer rim 118 extending around the periphery of the annular ring 102 to help reduce cellular proliferation onto the lens 200.

With specific reference to FIG. 3, the lens 200 of the modular IOL includes an optic portion 202 and one or more tabs 204 and 206. As shown, tab 204 is fixed, whereas tab 206 may be actuated. Fixed tab 204 may include a thru hole 208 so that a probe 450 (e.g., Sinskey hook) or similar device may be used to engage the hole 208 and manipulate the tab 204. Actuatable tab 206 may be actuated between a compressed position for delivery into the hole 104 of the base 100, and an uncompressed extended position (shown) for deployment into the recess 112 of the base 100, thus forming an interlocking connection between the base 100 and the lens 200. It also is contemplated that actuatable tab 206 may be inserted into recess 112, and may be actuated between the compressed position to facilitate entry of fixed tab 104 into recess 112, and the uncompressed extended position to insert fixed tab 104 further into recess 112 to form the interlocking connection between base 100 and lens 200.

Actuatable tab 206 may include two members 210 and 212, each with one end connected to the peripheral rim 214 around the optic 202, and the other end free, thus forming two cantilever springs. The rim 214 may have an outside diameter that is greater than the inside diameter of the posterior rim 108 of the base 100 such that the lens 200 doesn't fall through the opening 104 of the base 100 and such that the lens 200 is circumferentially supported around its perimeter by the posterior rim 108 of the base 100. A notch 216 may be formed in the peripheral rim 214 between the two members 210 and 212 to add hinge-like flexibility. A notch 218 may be provided in the fixed tab 204 to provide access for a probe (e.g., Sinskey hook) or similar device to manipulate the fixed tab 204 into the recess 112 in the base 100. The free ends of members 210 and 212 may extend in opposing directions. It also is contemplated that one or more of members 210 and 212 may be curved to facilitate bending. For example, radially-outer surfaces of members 210 and 212 may be convex, while radially-inner surfaces of members 210 and 212 may be concave.

In general, when the base 100 and lens 200 are assembled, the features may be configured such that the mid-plane of the optic 202 is parallel with the mid-plane of the base 100, and the central (anterior-posterior) axis of the optic 202 is coincident and collinear with the central (anterior-posterior) axis of the base 100. Assuming anatomic symmetry of the native lens capsule and centration of the base 100 in lens capsule, this configuration essentially aligns the central axis of the optic 202 with the central (anterior-posterior) axis of the capsular bag, thus providing centration of the optic 202. However, there may be instances where the visual (foveal) axis is not aligned with the anatomic (pupillary axis), wherein the difference is called angle of kappa. In such instances, it may be desirable to offset the central axis of the optic 200 relative to the base 100, thus providing de-centration. This may be accomplished, for example, by configuring the tabs 204 and 206, the recess 112 and/or the haptics 106 such that the central (anterior-posterior) axis of the optic 202 is laterally (nasally or temporally) offset relative to the central (anterior-posterior) axis of the base 200. By way of example, not limitation, the lateral walls defining the recess 112 in the base may be offset relative to the haptics 106 so that the central axis of the optic 202 is offset. Different offsets could be provided, for example, 0.5 mm through 2.0 mm at 0.5 mm increments. Angular orientation marks on the base 100 and lens 200 may be provided to indicate the direction of the offset (nasally or temporally). Similarly, the mid-plane of the assembled base 100 and optic 200 may be tilted relative to the equatorial plane of the native capsular bag. To compensate for this tilt, for example, the tabs 204 and 206, the recess 112 and/or the haptics 106 may be configured such that the mid-plane of the optic 202 is counter-tilted.

As will be described in more detail later, the lens 200 may be rolled about axis 220 or axis 222, for example, for purposes of delivery via an injector. Axes 220 and 222 essentially bisect the lens 200. Axis 220 passes through the center of the optic 202 and through the center of the two tabs 204 and 206. Axis 222 passes through the center of the optic 202 in between the two tabs 204 and 206 such that the diametrically opposed tabs 204 and 206 are on either side of the axis 222.

The base 100 and lens 200, including the alternative embodiments described herein, may be formed by cryogenically machining and polishing hydrophobic acrylic material. Optionally, the base 100 may be manufactured by forming two (anterior and posterior) components and adhesively connecting them together. For example, the two components may be cryogenically machined hydrophilic acrylic connected together by a U.V. curable adhesive. Alternatively, the two components may be formed of different materials adhesively connected together. For example, the anterior component may be formed of hydrophilic acrylic which does not adhere to ocular tissue, and the posterior component may be formed of hydrophobic acrylic which does adhere to ocular tissue.

As a further alternative, the base 100 may be manufactured by cryogenic machining the first component and over-molding the second component. The first component may include geometric features that become interlocked when over-molded, thus mitigating the need for adhesive to connect the components. For example, the base 100 may be manufactured by cryogenic machining of hydrophilic acrylic to form the posterior component, and over-molding the anterior component of a moldable material such as silicone.

While hydrophobic acrylic renders the base 100 and lens 200 visible using optical coherence tomography (OCT), it may be desirable to incorporate a material that enhances OCT visualization. Example "OCT-friendly" materials include but are not limited to polyvinyl chloride, glycol modified poly (ethylene terephthalate) (PET-G), poly (methyl methacrylate) (PMMA), and a polyphenylsulfone, such as that sold under the brand name RADEL™, as described in U.S. Patent Application Publication 2013/0296694 to Ehlers et al., which is incorporated herein by reference. Such OCT-friendly materials may be applied to or incorporated into a portion of the base 100 or lens 200. By way of example, a concentric ring of OCT-friendly material may be applied to each of the lower and upper rims 108/110. The rings may have different diameters to aid in detecting tilt of the base. Also by way of example, OCT-friendly material may be applied to the tabs 204/206 of the lens 200. This may aid in determining if the base 100 and lens 200 are correctly assembled in the eye. Points of OCT-friendly material may be applied to portions of the base 100 that line up to corresponding OCT-friendly points on the optic 200 to indicate proper assembly in the eye.

As an alternative to solid material, the base 100 and lens 200 may be made of hollow material that can be subsequently inflated in the eye. In this arrangement, the base 100 and lens 200 may be made from molded silicone, for example, and inflated with a liquid such as saline, silicone gel or the like using a syringe and needle. The needle may pierce the wall of the base 100 and lens 200 after implantation in the eye to inflate the components. The material may self-seal after removal of the needle. As an alternative to a hollow material, the base 100 and lens 200 may be formed of a sponge-like material such as silicone hydrogel that swells upon hydration. Both approaches allow the size of the corneal incision to be smaller, as the base 100 and lens 200 are delivered in an uninflated or unswelled state and subsequently inflated or swelled once inside the eye.

Figure 4A:
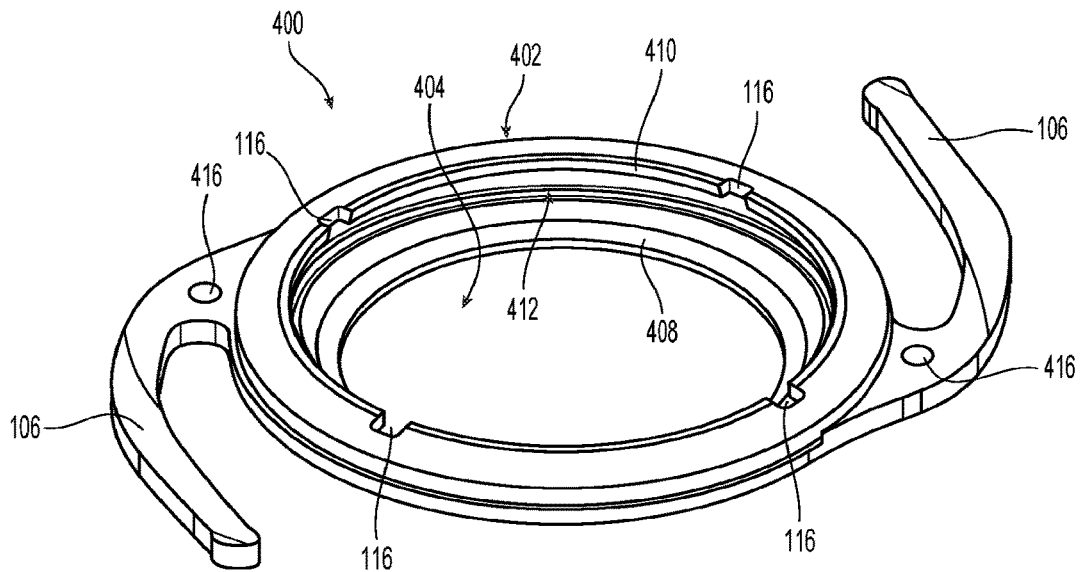
FIGS. 4A-4D are various views of an alternative base.
Figure 4B:
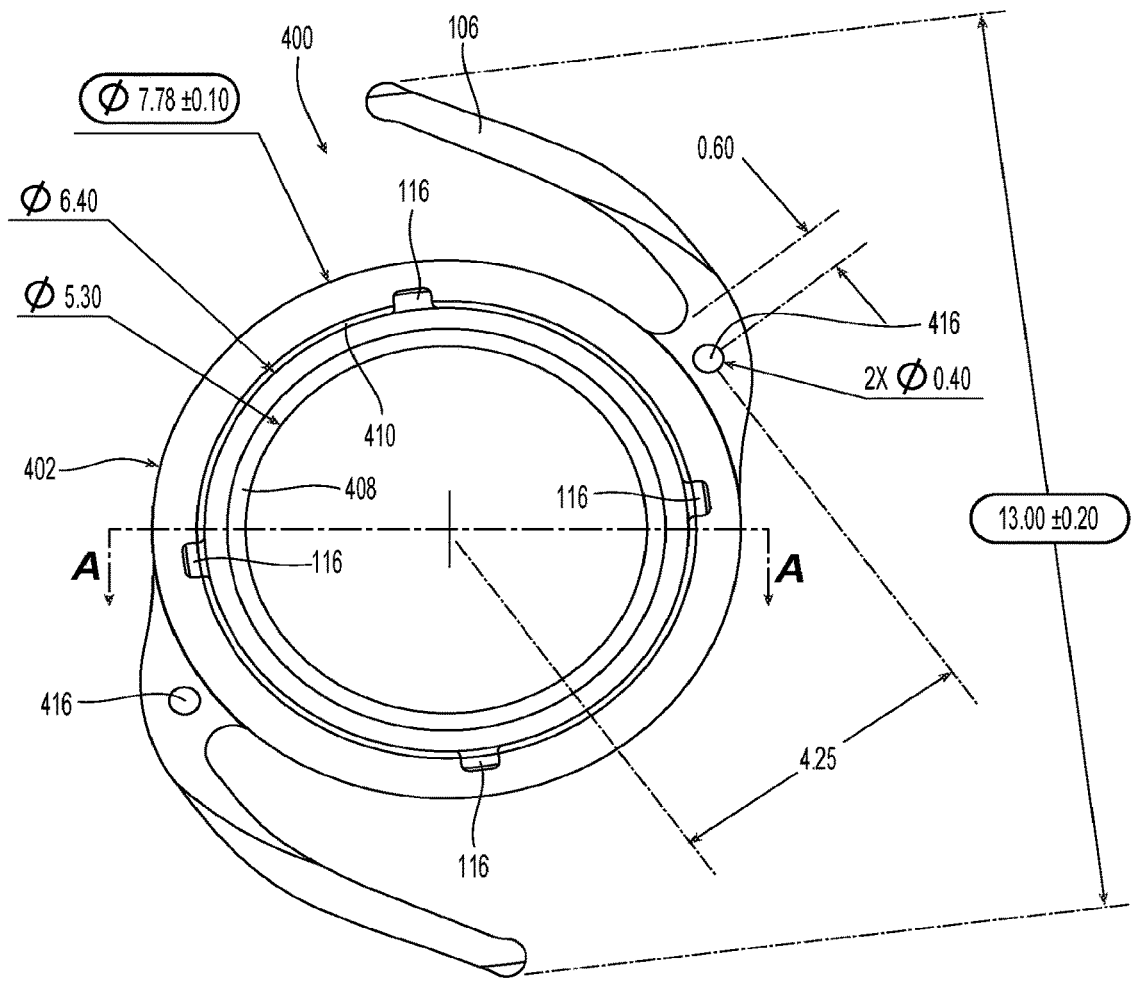
Figure 4C:
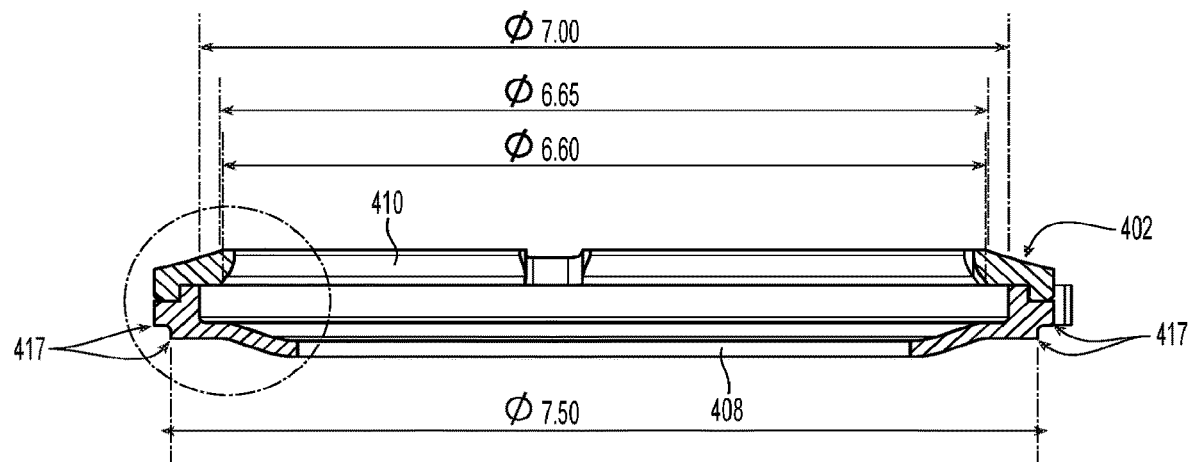
Figure 4D:
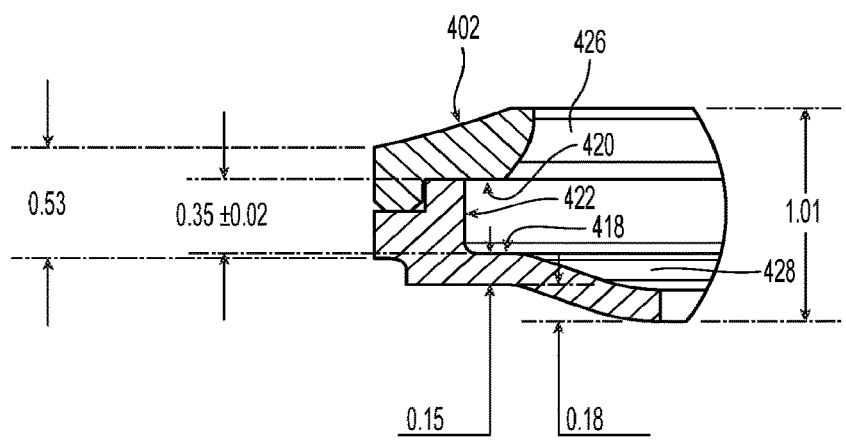

With reference to FIGS. 4A-4D, an alternative base 400 is shown. FIG. 4A is a perspective view, FIG. 4B is a top view, FIG. 4C is sectional view taken along line A-A in FIG. 4B, and FIG. 4D is a detailed sectional view circle C in FIG. 4C. Dimensions (mm) are given by way of example, not necessarily limitation. Alternative base 400 is similar to base 100 described with reference to FIG. 2 except as otherwise described below.

Alternative base 400 includes an annular ring 402 defining a center hole 404. A pair of haptics 106 extend radially outward from the annular ring 402. The annular ring 402 includes a lower rim 408, an upper rim 410 and an inward-facing recess 412, into which the lens 200 may be inserted to form a modular IOL. As will become apparent from the description with reference to FIGS. 4A-4D, the recess 412 of base 400 is sized and configured differently than the recess 112 of base 100.

The upper rim 410 of annular ring 402 may include one or more notches 116 to provide access for a probe (e.g., Sinskey hook) intra-operatively, which allows the base 400 to be more easily manipulated. The haptics 106 may include holes 416 adjacent the annular ring 402 for the same purpose as notches 116. A pair of square edges 417 may extend around the posterior periphery of the annular ring 402 to help reduce cellular proliferation (posterior capsular opacification or PCO) onto the lens 200.

With specific reference to FIG. 4D, the deep portion of the recess 412 may have a squared profile defined by horizontal posterior surface 418, a horizontal anterior surface 420 and a vertical lateral or outer surface 422. The recess may also include a flared anterior surface 426 extending radially inward and anteriorly outward from the horizontal anterior surface 420, and a flared posterior surface 428 extending radially inward and posteriorly outward from the horizontal posterior surface 418. The inside diameter of the posterior rim 408 may be smaller than the inside diameter of the anterior rim 410. With this arrangement, the lens 200 may be placed through the circular opening defined by the anterior rim 410 to land or rest upon the posterior rim, and the flared anterior wall 426 together with the flared posterior wall 428 may act as a funnel to guide the tabs 204 and 206 of the lens 200 into the deep portion of the recess 412. When fully seated in the recess 412, the horizontal posterior wall 418, the horizontal anterior wall 420 and the vertical lateral wall 422 form a keyed geometry with the corresponding horizontal and vertical sides of the tabs 204 and 206 to limit movement of the lens 200 relative to the base 400 in anterior, posterior and radial directions.

Figure 5A:
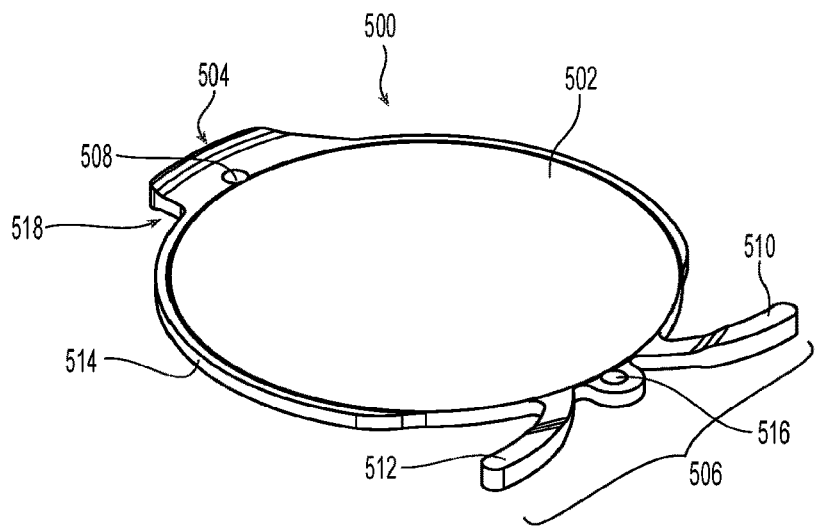
FIGS. 5A-5E are various views of an alternative lens.
Figure 5B:
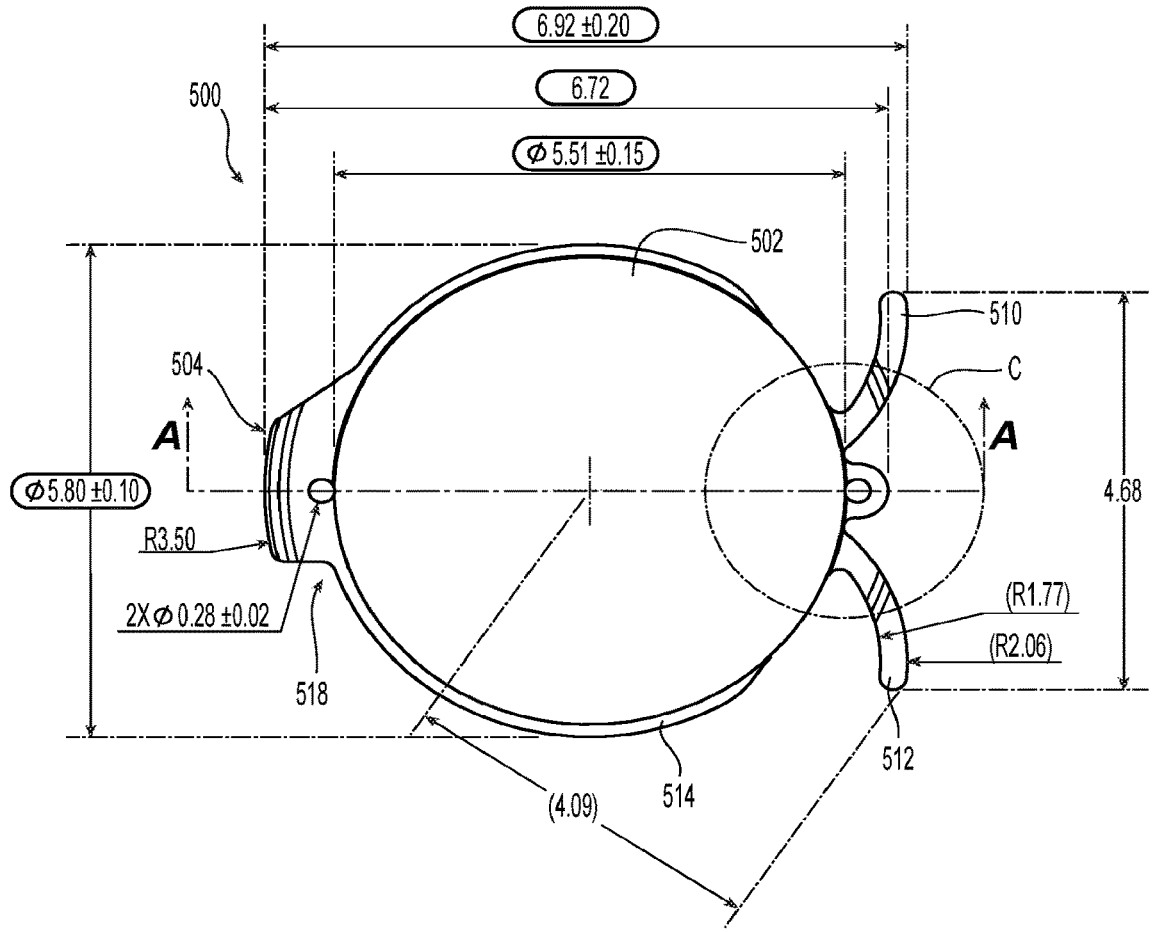
Figure 5C:
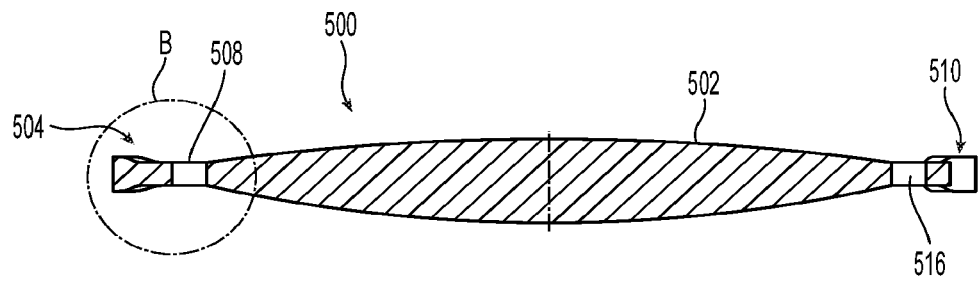
Figure 5D:
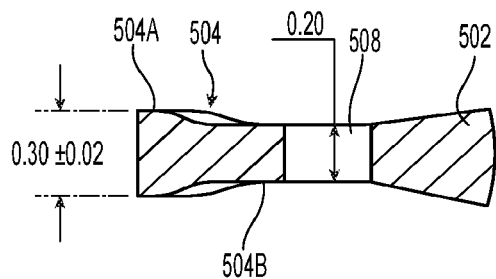
Figure 5E:
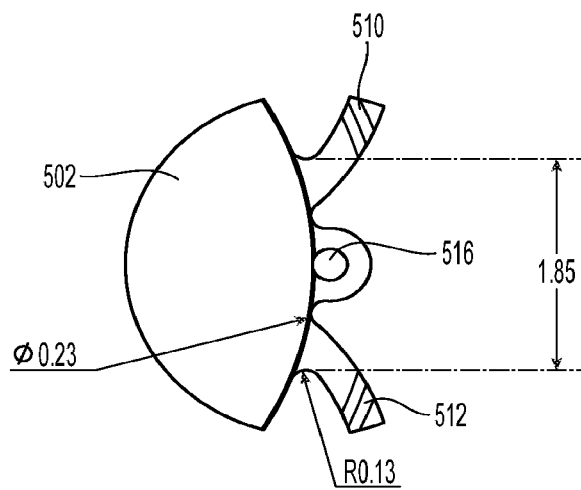

With reference to FIGS. 5A-5E, an alternative lens 500 is shown. FIG. 5A is a perspective view, FIG. 5B is a top view, FIG. 5C is sectional view taken along line A-A in FIG. 5B, FIG. 5D is a detailed sectional view of circle B in FIG. 5C, and FIG. 5E is a detailed top view of circle C in FIG. 5B. Dimensions (mm) are given by way of example, not necessarily limitation. Alternative lens 500 is similar to lens 200 described with reference to FIG. 3 except as otherwise described below.

The lens 500 may include an optic portion 502 and one or more tabs 504 and 506. As shown, tab 504 is fixed, whereas tab 506 may be actuated. Fixed tab 504 may include a thru hole 208 so that a probe (e.g., Sinskey hook) or similar device may be used to engage the hole 208 and manipulate the tab 504. Actuatable tab 506 may be actuated between a compressed position for delivery into the hole 404 of the base 400, and an uncompressed extended position (shown) for deployment into the recess 412 of the base 400, thus forming an interlocking connection between the base 400 and the lens 500. It also is contemplated that actuatable tab 506 may be inserted into recess 412, and may be actuated between the compressed position to facilitate entry of fixed tab 504 into recess 412, and the uncompressed extended position to insert fixed tab 504 further into recess 412 to form the interlocking connection between base 400 and lens 500.

Actuatable tab 506 may include two members 510 and 512, each with one end connected to the edge of the optic 502, and the other end free, thus forming two cantilever springs. A rim 514 may extend around the perimeter of the optic 502, terminating shy of the springs 510 and 512, thus allowing the springs 510 and 512 to fully compress against the edge of the optic 502. The rim 514 of the lens 500 may have an outside diameter that is greater than the inside diameter of the posterior rim of the base 400 such that the lens 500 doesn't fall through the opening 404 of the base 400 and such that the lens 500 is circumferentially supported around its perimeter by the posterior rim 408 of the base 400. A gusset with a guide hole 516 may be disposed between the two members 510 and 512 to facilitate manipulation by a probe. Similarly, a guide hole 508 may be provided in the fixed tab 504 to provide access for a probe (e.g., Sinskey hook) or similar device to manipulate the fixed tab 504 into the recess 412 in the base 400. A notch 518 may be provided in the fixed tab 504 to provide asymmetry as a visual indicator that the anterior side is up (rather than down) when the notch is counter-clockwise of the hole 508.

As seen in FIG. 5C, the anterior and posterior sides of the optic 502 may have convex radii corresponding to the desired power (Diopter) of the optic. The fixed tab 504 and the spring tabs 510 and 512 may have a flared cross-section as shown. More specifically, and as better seen in the detailed view shown in FIG. 5D, the fixed tab 504 extends radially outward from the optic 502 from a thinner inner portion 504B to a flared thicker outer portion 504A. Hole 508 may extend through thinner inner portion 504B. The outermost profile of the thicker portion 504A has a squared profile with an anterior horizontal side, a posterior horizontal side, and a lateral or outer vertical side that are keyed to the recess 412 as described previously to minimized anterior-posterior and radial/lateral movement of the lens 500 relative to the base 400. The thicker portion 504A also provides for improved engagement with the plunger of an injector to mitigate jamming of the lens 500 in the injector. The thinner portion 504B also provides an anterior and a posterior offset from the surfaces defining the recess 412 of the base 400, thereby mitigating adhesion between the lens 500 and the base 400. The same flared configuration and associated advantages also applies to each of the spring tabs 510 and 512 as shown.

Commercially available IOLs typically have an equatorial diameter (excluding haptics) of about 6 mm, an anterior-posterior thickness of about 0.2 mm at 6 mm diameter and 0.7 mm at the center, providing an overall volume of about 12 mm3. Lens 500 is similarly dimensioned, but the base 400 adds substantially more volume. The base 400 may have an equatorial diameter (excluding haptics) of about 7.8 mm, an anterior-posterior thickness of about 1 mm, providing an overall volume of about 26 cubic millimeters [13.4 mm3 base, 12.5 mm3 optic] when the lens is disposed into the base. Thus, the size of the combined base 400 and lens 500 is volumetrically much larger than conventional IOLs available on the market. This relatively larger volume is intended to fill the capsular bag more like a natural lens, thus increasing the stability of the base 400 and lens 500 and reducing post-operative migration due to the bag collapsing around the base 400. By way of comparison, a typical natural lens has an equatorial diameter of about 10.4 mm, an anterior-posterior dimension of about 4.0 mm for a corresponding volume of about 180 mm3. Due to anatomic variability, a natural lens may have a volume ranging from 130 mm3 to 250 mm3. Thus, the base 400 plus the lens 500 consumes greater than 10% (about 20% to 10.4%) of the volume of the bag after the natural lens has been extricated, whereas a conventional IOL consumes less than or equal to 10% (about 10% to 5%) of the volume of the bag. In other words, the base 400 plus the lens 500 consumes about twice the volume of the bag compared to a conventional IOL.

Figure 6A:
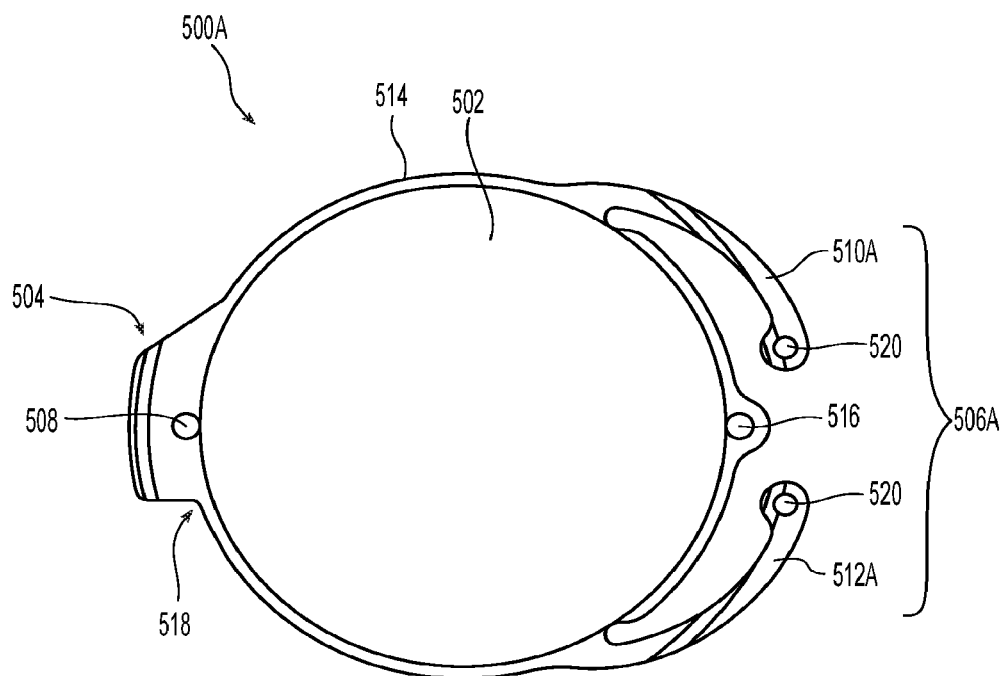
FIGS. 6A-6D are top views of various iterations of the alternative lens.
Figure 6B:
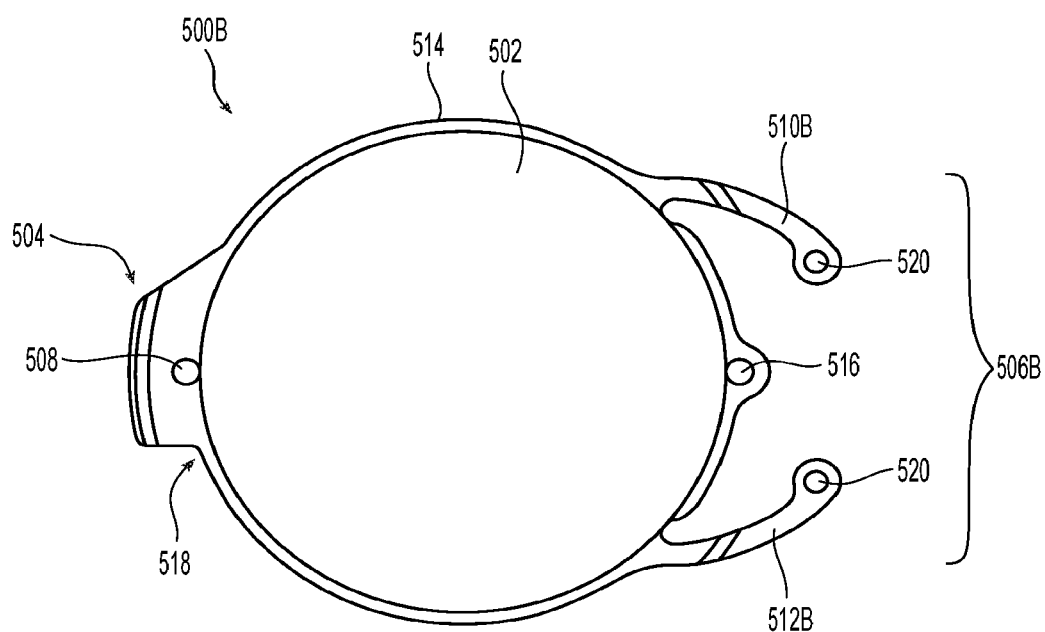

With reference to FIGS. 6A-6D, various iterations of lens 500 are shown in schematic top views. In FIG. 6A, the lens 500A includes actuatable tab 506A with spring tabs 510A and 512A that include a hole 520 for manipulation by a probe or similar device. The spring tabs 510A and 512A are relatively longer than the embodiment described with reference to FIGS. 5A-5E and extend in a radially outward direction from the optic 502 with the corresponding ends extending toward each other. This allows easy manipulation of the actuatable tab 506A such that the fixed tab 504 may be inserted into the recess 412 of the base 400 and then the spring tabs 510A and 512B may be individually manipulated and tucked into the recess 412 using a probe placed in holes 520. The holes 520 may be positioned and dimensioned on the spring tabs 510A and 512A such that they are partially visible when seated in the recess 412. In other words, if the holes 520 are completely visible, then the spring tabs 510A and 512A are anterior to the anterior rim 410 of the base 400, if the holes 520 are not visible, then the spring tabs 510A and 512A are posterior to the posterior rim 408 of the base 400, and if the holes 520 are partially visible (e.g., half visible), then the spring tabs 510A and 512A are properly seated in the recess 412 of the base 400. Since the ends of the spring tabs 510A and 512A are in closer proximity than the ends of the arms 510 and 512 of lens 500, a smaller visual area is required to confirm the actuatable tab 506A is in the recess 412 of the base 400 when viewed under a microscope intra-operatively. FIG. 6B illustrates a similar lens 500B but with shorter spring tabs 510B and 512B to provide more spring force and stability in the recess 412 of the base 400.

Figure 6C:
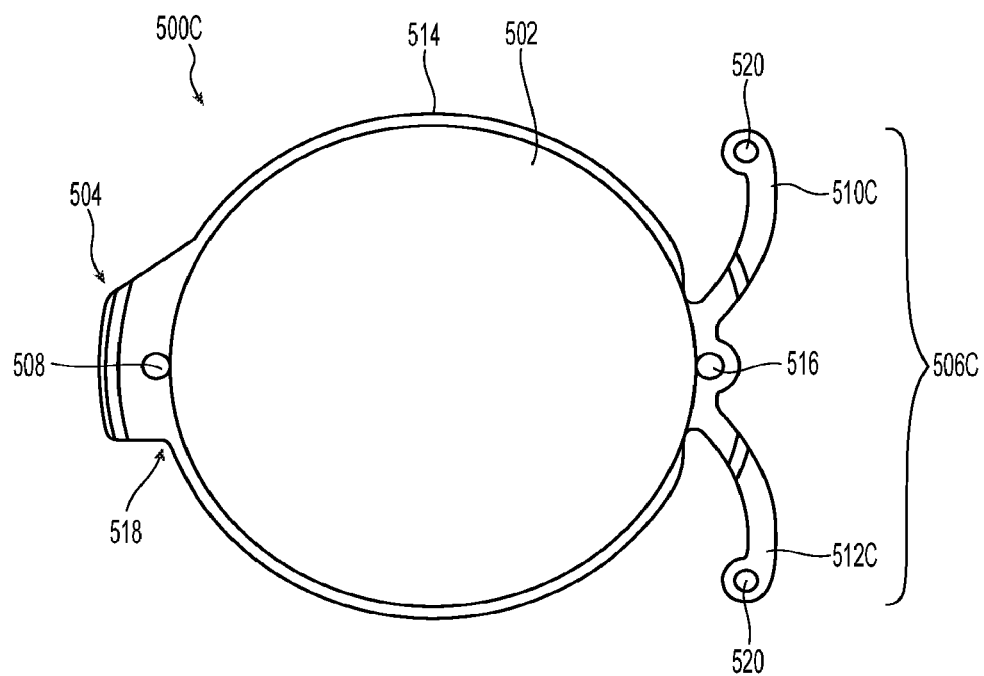
Figure 6D:
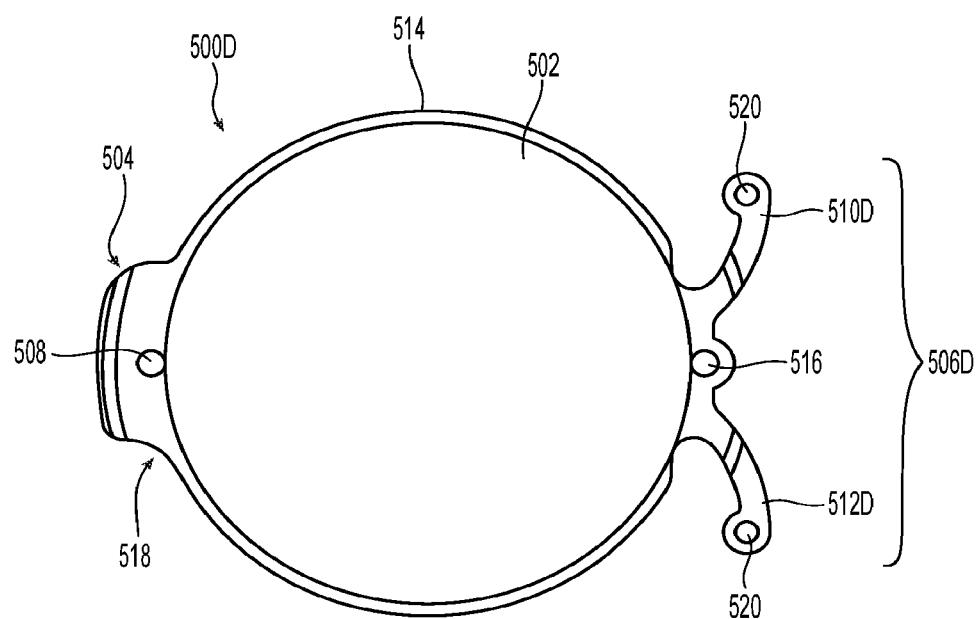

In FIG. 6C, the actuatable tab 506C includes spring tabs 510C and 512C that extend in a radially outward direction from the optic 502 with corresponding ends extending away from each other. By extending away from each other, the spring tabs 510C and 512C provide a wider base of contact with the recess 412 of the base 400, thereby mitigating tilt of the lens 500C within the base. FIG. 6D illustrates a similar lens 500D but with spring tabs 510D and 512D that have a wider attachment to the optic 502 to provide more spring force and stability in the recess 412 of the base 400.

Figure 7:
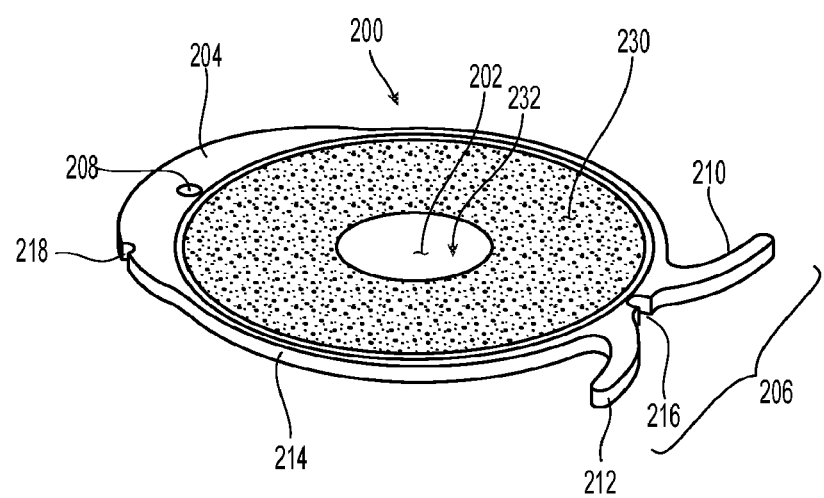
FIG. 7 is a perspective view of a pinhole lens according to the present disclosure.

With reference to FIG. 7, the optic portion 202 of the lens 200 may include an opaque ring 230 defining a small 1.0-2.0 mm center aperture 232 (pinhole) to allow only focused light into the eye to increase depth of focus. The opaque ring 230 may comprise a dark mask applied to the surface of the optic 202, or other surface treatment to partially or completely block visible light. The surface treatment may be applied to the optic 202 prior to implantation (i.e., at time of manufacture), or may be applied post operatively (i.e., after implantation) to customize the characteristics (e.g., size and position) of the aperture 232 to the needs of the patient. The surface treatment may comprise laser etching or frosting of the surface of the optic 202 to define or modify the opaque ring 230. Alternatively, the surface treatment may comprise selective activation or deactivation of a chromophore on or embedded in the optic 202 to change the color or contrast (lighter or darker) thereof and thereby define or modify the aperture 232. The aperture 232 may be centered on the optic 202 as shown, or it may be off-center such that the lateral position of the aperture 232 may be adjusted relative to the visual axis by rotating the lens 200 relative to the base 100.

Figure 8A:
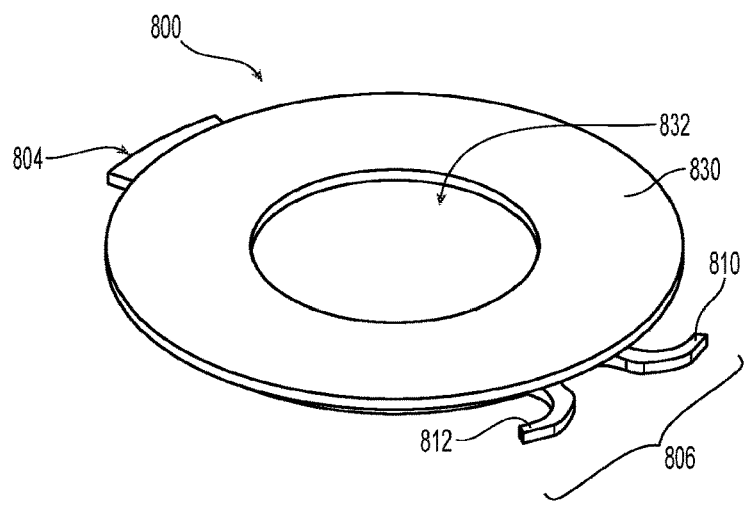
FIGS. 8A-8D are various views of an alternative pinhole component according to the present disclosure.
Figure 8B:
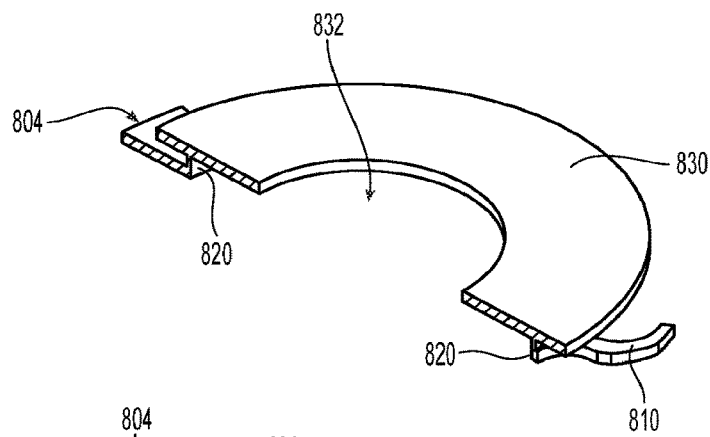
Figure 8C:
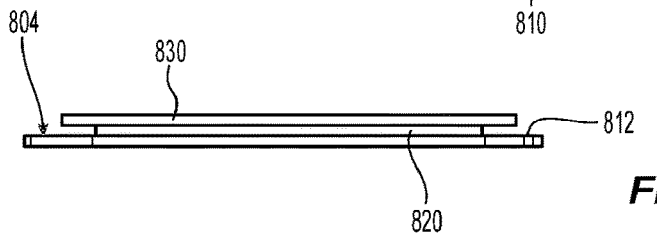
Figure 8D:
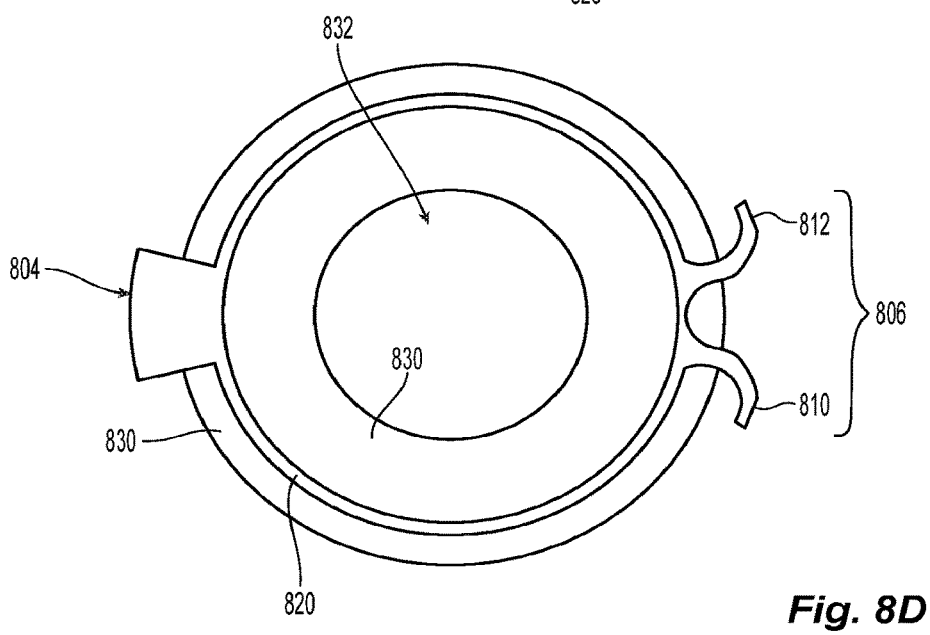

Alternatively, the opaque ring may comprise a third (separate) component 800 with a pinhole as shown in FIGS. 8A-8D. FIG. 8A is a perspective view, FIG. 8B is a sectional view taken along line A-A in FIG. 8A, FIG. 8C is a side view, and FIG. 8D is a bottom view of the pinhole component 800. Pinhole component 800 may include an opaque anterior ring 830 defining a small 1.0-2.0 mm center aperture 832 (pinhole) to allow only focused light into the eye to increase depth of focus. A fixed tab 804 may extend radially outward from a posterior stand-off ring 820. Similarly, an actuatable tab 806 comprising spring members 810 and 812 may extend radially outward from stand-off ring 820 in the other diametric direction. Posterior stand-off ring 820 may have a height slightly greater than the thickness of the lens 200 such that the tabs 804 and 806 are aligned with the recess 112 on the base 100 when the pinhole component 800 rests on the anterior side of the lens 200. This configuration allows the pinhole component 800 to be positioned over the lens 200 with both the lens 200 and the pinhole component 800 connected to the base 100. The pinhole component 800 may be attached to the base 100 such that the tabs 804 and 806 of the pinhole component 800 are positioned offset (e.g., 90 degrees) from the tabs 204 and 206 of the lens 200. In other words, tabs 804 and 806 of the pinhole component 800 utilize portions of the recess 112 of the base 100 that are unoccupied by the tabs 204 and 206 of the lens 200. Optionally, a similar configuration may be used for a third component comprising a toric lens, a multifocal lens, a telescopic lens, etc.

Figure 9:
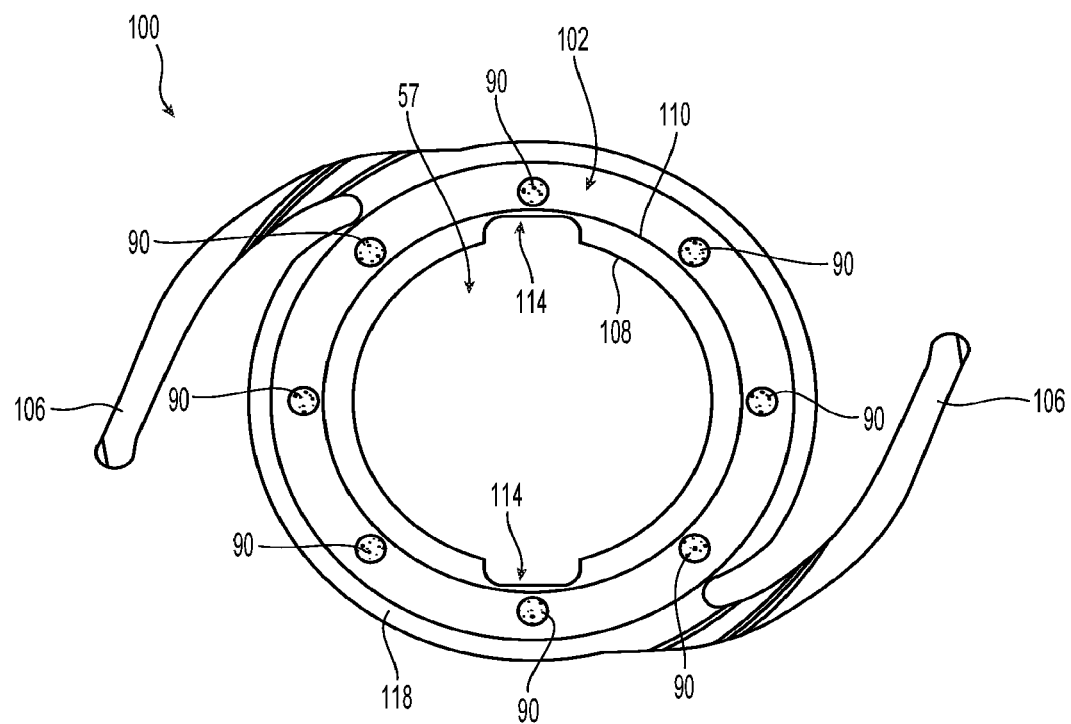
FIG. 9 is a top view of a base with drug delivery capability according to the present disclosure.

Optionally, drugs may be incorporated into or carried by the base 100 as shown in FIG. 9. Using the base 100 as a carrier for drugs, as opposed to the lens 200, has a number of advantages. For example, it avoids any interference the drug or drugs may have with the optical performance of the lens 200. Also, because the base 100 doesn't require tumbling as part of the manufacturing process like the lens 200 does, drugs carried by the base 100 aren't exposed to potential damage. Drugs may be incorporated into the base 100 by connecting one or more separate drug carriers to the base 100, having the material of the base 100 act as a carrier for the drug (e.g., like a sponge), incorporating one or more drug-eluting materials into the base 100, or incorporating one or more refillable reservoirs into the base 100 that carry the drug. One or multiple portions of the base 100 may carry the drug or drugs, and these portions may be separate from each other, to avoid interaction between different drugs, for example. The portion or portions of the base 100 carrying the drug may be selectively activated by light or thermal energy (e.g., laser, UV light, etc.) to release the stored drug or drugs all at once or in a series of releases over time.

Examples of clinical indications for such drugs include wet or dry macular degeneration, open or close angle glaucoma, uveitis, posterior capsular opacification, post-op management after cataract surgery, etc. Examples of drugs that may be used for wet macular degeneration include aflibercept, bevacizumab, pegaptanib, ranibizumab, steroids, and aptamers. Examples of drugs that may be used for dry macular degeneration include complement factors, antioxidants and anti-inflammatory agents. Examples of drugs that may be used for open angle glaucoma include brimonidine, latanoprost, timolol, pilocarpine, brinzolamide and other drugs in the general categories of beta blockers, alpha agonists, ROCK Inhibitors, adenosine receptor agonsists, carbonic anhydrase inhibitors, adrenergic and cholinergic receptor activating agents, and prostaglandin analogues. Examples of drugs that may be used for uveitis include methotrexate, antibodies, dexamethasone, triamcinolone, and other steroid agents. Examples of drugs that may be used for posterior capsular opacification include anti-proliferative, anti-mitotic, anti-inflammatory, and other medications that would inhibit the spread of lens epithelial cells. Examples of drugs that may be used for post-op management after cataract surgery include antibiotics such as fluoroquinolones, non-steroidal agents such as ketorolacs, and steroids such as prednisolones. Other medications that may be used to treat various ocular diseases and conditions include: anti-fibrotic agents, antiinflammatory agents, immunosuppressant agents, anti-neoplastic agents, migration inhibitors, anti-proliferative agents, rapamycin, triamcinolone acetonide, everolimus, tacrolimus, paclitaxel, actinomycin, azathioprine, dexamethasone, cyclosporine, bevacizumab, anti-VEGF agents, anti-IL-1 agents, canakinumab, anti-IL-2 agents, viral vectors, beta blockers, alpha agonists, muscarinic agents, steroids, antibiotics, non-steroidal antiinflammatory agents, prostaglandin analogues, ROCK inhibitors, nitric oxide, endothelin, matrixmetalloproteinase inhibitors, CNPA, corticosteroids, and antibody-based immunosuppressants. These drugs may be used individually or in combination, depending on the patient's particular clinical indication.

Also, the portion or portions of the base 100 carrying the drug or drugs may face a particular direction or directions while other directions are masked or blocked to increase the concentration of the drug on a specific portion of the lens capsule. For example, posterior ocular structures may be the focus of drug delivery (e.g., to mitigate macular degeneration), and/or anterior ocular structures may be the focus of drug delivery (e.g., to deliver glaucoma drugs adjacent the angle, to deliver drugs for uveitis or post-op management after cataract surgery).

By way of example, FIG. 9 shows a top (anterior) view of the base 100, which incorporates one or more drug carriers 90. As shown, the drug carriers 90 are spaced around the circumference of the anterior side of the body of the base 100. The drug carriers 90 may comprise a refillable reservoir (e.g., silicone vessel), an eluting porous material (e.g., biocompatible sponge), a biodegradable or bioerodable material (e.g., PLGA), etc. The reservoir may also be targeted to expose drugs to the aqueous environment through laser, UV light, RF signal, magnetic manipulation or other methods for remotely removing a barrier to diffusion. The carriers 90 may be placed on the surface of the base 100, or embedded, for example. To focus the delivery of drugs to a particular area of the eye, the carriers 90 may be exposed on one side (e.g., the anterior side as shown) while the material of the base 100 covers the other sides.

Figure 10A:
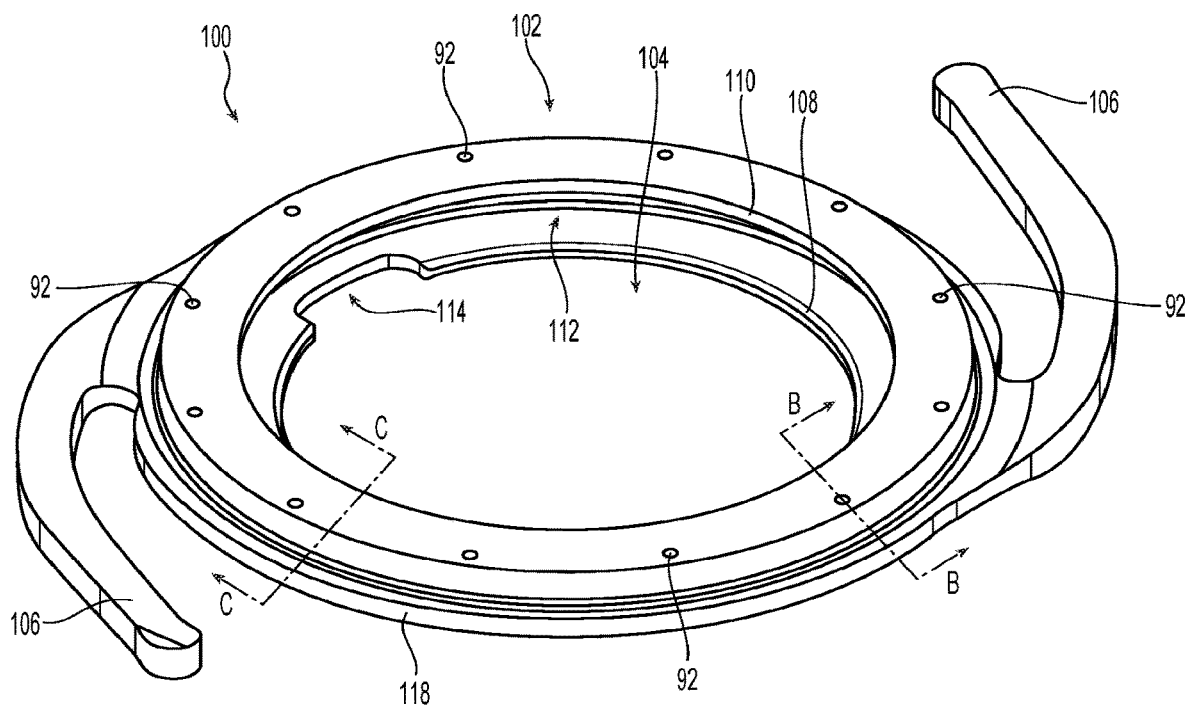
FIGS. 10A-10C are various views of an alternative base with drug delivery capability according to the present disclosure.
Figure 10B:
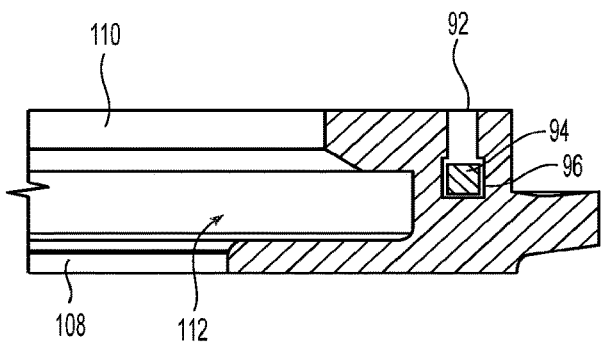
Figure 10C:
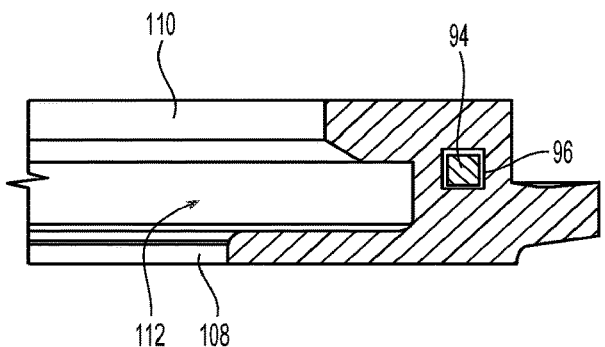

An alternative drug carrying base 100 is shown in FIGS. 10A-10C. FIG. 10A is a perspective view, FIG. 10B is a sectional view taken along line B-B in FIG. 10A, and FIG. 10C is a sectional view taken along line C-C in FIG. 10A. As seen in FIGS. 10B and 10C, the base 100 may include an internal channel 96 extending around the circumference of the annular ring 102. The internal channel 96 is in fluid communication with the exterior of the base 100 via a series of ports 92 that may be equally distributed around the anterior side of the annular ring 102. A ring 94 of material may be disposed in the channel 96. The ring 94 of material may have a dehydrated volume that is less than the volume of the channel 96, and a hydrated volume that is greater than its dehydrated volume up to the volume of the channel 96. The ring 94 material may comprise, for example, high equilibrium water content (EWC) silicone hydrogel, or other similar hydratable or sponge-like material. In use, prior to implantation, the base 100 with dehydrated ring 94 may be soaked in a fluid containing the desired drug or drugs, such as a steroid and an NSAID, for example. The ports 92 would allow the drug-carrying fluid to flow to the dehydrated ring 94 which would cause the dehydrated ring 94 to increase in volume (swell) as it became hydrated with the drug-carrying fluid. The hydrated ring 94 may then occupy the entire volume of the channel 96. When the base 100 is implanted, the aqueous humor of the eye contacts the ring of hydrated material 96 adjacent the ports 92, rather than bathing the entire ring 94 in the channel 96. Thus, drug elution from the ring 94 into the eye may be controlled by the number and size of ports 92, which may be selected to achieve the desired elution rate for a given drug or combination of drugs.

In general, the modular IOL, comprising the assembled base 100 and lens 200, including the alternative embodiments described herein, allows for the lens 200 to be adjusted or exchanged while leaving the base 100 in place, either intra-operatively or post-operatively. Examples of instances where this may be desirable include, without limitation: exchanging the lens 200 to correct a suboptimal refractive result detected intra-operatively; exchanging the lens 200 to correct a suboptimal refractive result detected post-operatively (residual refractive error); rotationally adjusting the lens 200 relative to the base 100 to fine tune toric correction; laterally adjusting the lens 200 relative to the base 100 for alignment of the optic with the true optical axis (which may not be the center of the capsular bag); and exchanging the lens 200 to address the changing optical needs or desires of the patient over longer periods of time. Examples of the latter instance include, but are not limited to: an adult or pediatric IOL patient whose original optical correction needs to be changed as s/he matures; a patient who wants to upgrade from a monofocal IOL to a premium IOL (toric, multifocal, accommodating or other future lens technology); a patient who is not satisfied with their premium IOL and wants to downgrade to monofocal IOL; and a patient who develops a medical condition where an IOL or a particular type of IOL is contra-indicated.

Figure 11:
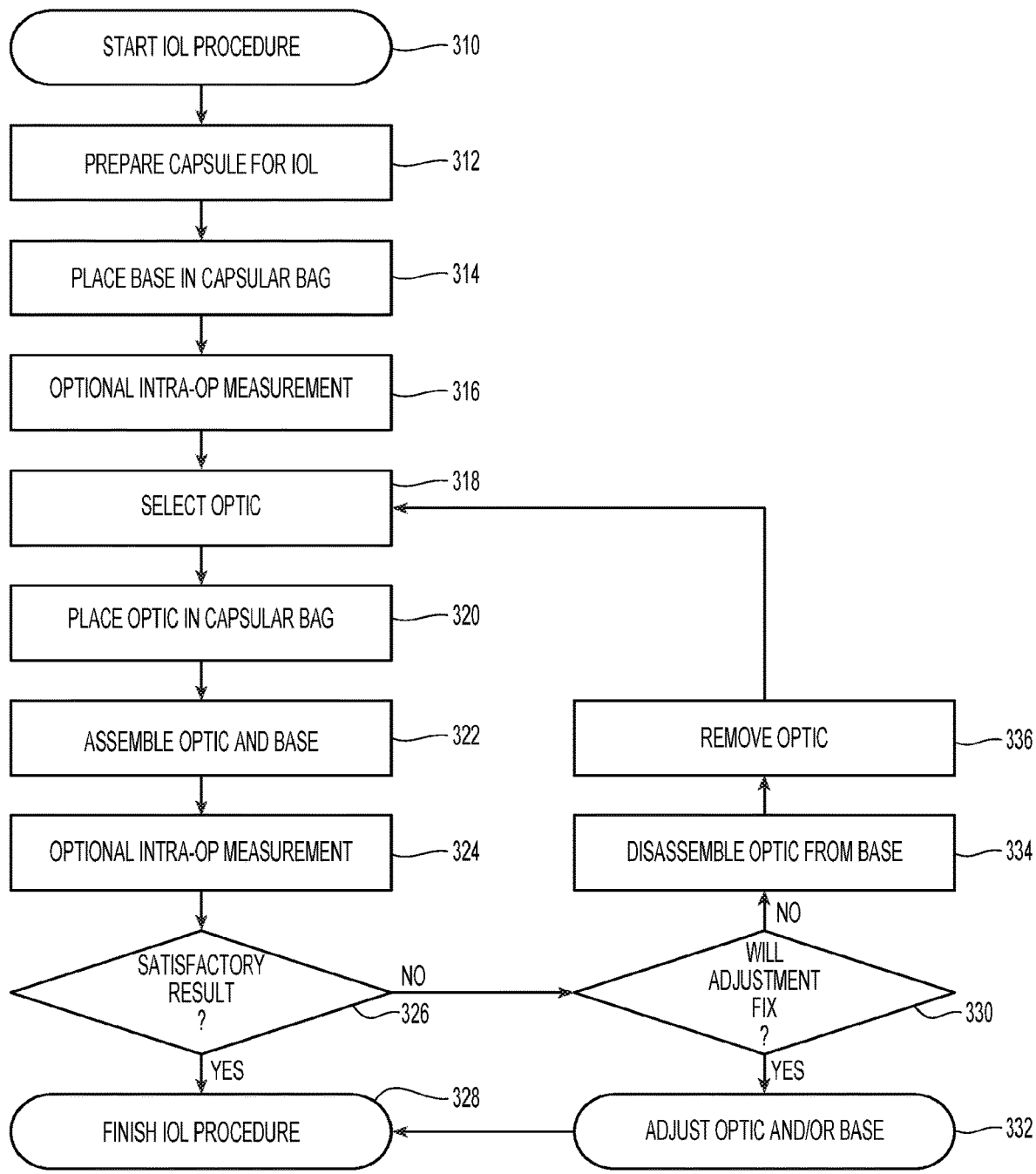
FIG. 11 is a flow chart showing an example procedure for using a modular IOL.

FIG. 11 illustrates an example of a procedure for implanting a modular IOL. In this example, intra-operative measurements may be made to select the desired lens 200 and/or to determine if an intra-operative adjustment or exchange is needed. The IOL implant procedure, such as cataract surgery, may be started 310 according to conventional practice. The native lens capsule may then be prepared 312 to receive a modular IOL using conventional steps such as making corneal access incisions, creating a capsulorhexis in the anterior capsular bag and removing the cataract lens by phacoemulsification or other means. The base 100 is then placed 314 in the capsular bag. At this point, an intra-operative measurement may be performed 316 to determine a position of the base 100 relative to anatomical structures. This information may be used, for example, to adjust the position of the base 100 and/or to aid in selection of the desired power of the optic portion 202 of the lens 200.

By way of specific example, optical coherence tomography (OCT) may be used to measure the effective base position (EBP) along the visual axis which will determine the effective lens position (ELP) once the lens 200 is connected to the base 100. Because ELP influences refractive outcome, EBP information may be used to select a lens 200 with the appropriate dioptric power. This may reduce residual refractive error, particularly because EBP is relatively stable post-operatively. OCT may also be used to detect de-centration and tilt of the base 100 so that adjustments thereto may be made intra-operatively. As described elsewhere herein, the base 100 may incorporate material to enhance OCT visualization.

Optionally, a temporary lens 200 may be placed in the eye and connected to the base 100 prior to OCT measurement. This may be helpful if the iris is small making OCT visualization of the base 100 challenging. The temporary lens 200 may be very thin (e.g., 0-2 diopters) allowing it to be easily removed after the OCT measurement is complete. As an alternative to a thin temporary lens, a thin disc of OCT reflective material may be placed on or connected to the base 100 prior to OCT measurement and subsequently removed.

The lens 200 is then placed 320 in the capsular bag. The base 100 and lens 200 are then assembled 322 as described in more detail hereinafter. At this point, an intra-operative measurement may be performed 324 to determine if the base 100 and lens 200 are correctly assembled, to determine the position of the assembled base 100 and lens 200 relative to anatomical structures, and/or to determine if the optical correction is satisfactory 326.

For example, OCT may be used to determine if the tabs 204 and 206 of the lens 200 are in the recess 112 of the base, and if necessary, steps may be taken to correctly assemble the lens 200 and the base 100. Additionally, or alternatively, OCT may be used to measure ELP, decentration or tilt, and if necessary, steps may be taken to adjust the position of the lens 200 and/or base 100. Additionally or alternatively, wave front aberrometry may be used to measure the optical result. If the optical result is determined 326 to be satisfactory, then the procedure may be finished 328 according to conventional practice. If the optical result is determined 326 to be unsatisfactory, a determination 330 is made as to whether adjustment (e.g., rotation, lateral shifting, etc.) of the lens 200 and/or base 100 will render the optical result satisfactory. If yes, then the adjustment is made 332 and the procedure is completed 328. If no, then the lens 200 is disassembled 334 from the base 100, removed 336 from the eye, and a new lens 200 is selected 318 and implanted following the same steps 320-328.

Figure 12A:
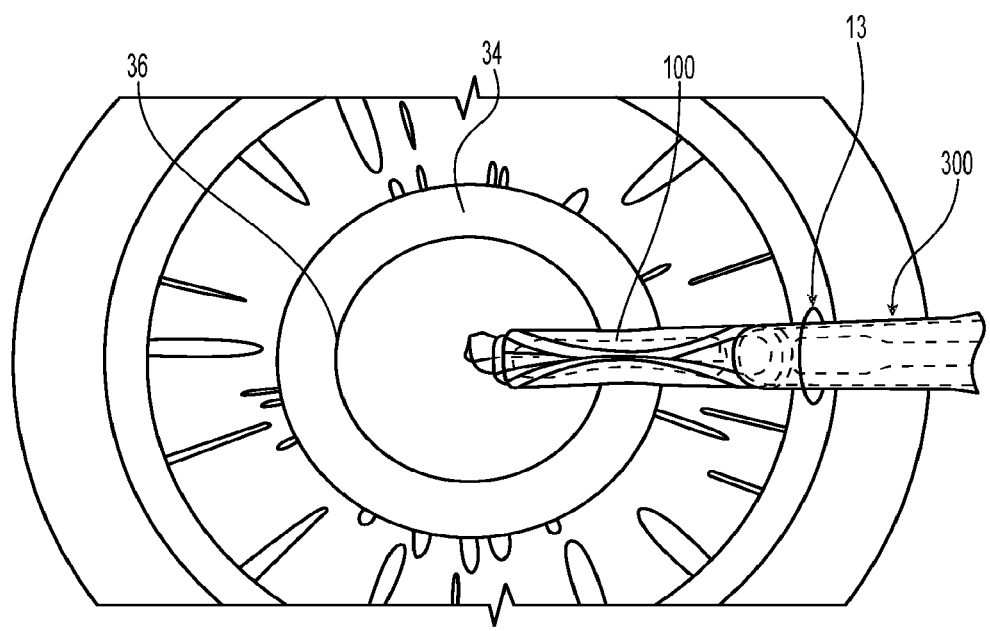
FIGS. 12A-12E show an exemplary technique for implanting a modular IOL.

FIGS. 12A-12D show techniques for implanting the modular IOL 100/200. As shown in FIG. 12A, the modular IOL may be implanted by initially delivering the base 100 into the capsular bag in a rolled configuration using an injector 300 (a.k.a., inserter or delivery tube) inserted through a corneal incision 13, through the capsulorhexis 36, and into the capsular bag 34. A conventional injector 300 (a.k.a., inserter) may be used to deliver the base 100 and lens 200. Examples of suitable injectors are described in U.S. Pat. No. 5,123,905 to Kelman, U.S. Pat. No. 4,681,102 to Bartell, U.S. Pat. No. 5,304,182 to Rheinish, and U.S. Pat. No. 5,944,725 to Cicenas.

Figure 12B:
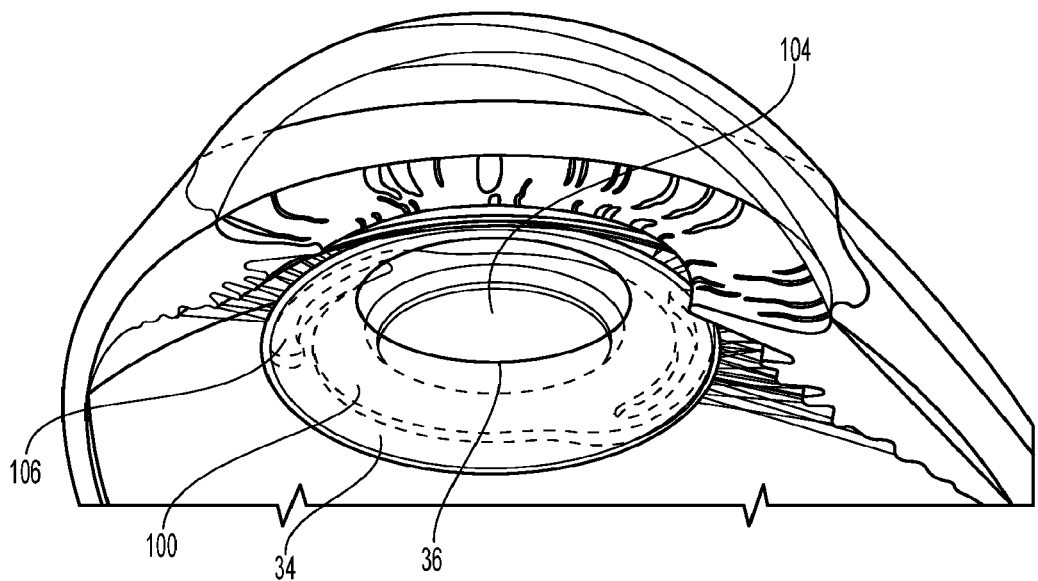

As shown in FIG. 12B, the base 100 may be ejected from the injector and allowed to unfurl. With gentle manipulation, the haptics 106 of the base 100 engage the inside equator of the lens capsule 34 and center the hole 104 of the base 100 relative to the capsulorhexis 36.

The lens 200 may also be delivered in a rolled configuration using an injector 300, positioning the distal tip thereof adjacent the base 100. The lens 200 may be ejected from the injector and allowed to unfurl. With gentle manipulation, the lens may be floated anteriorly of the base 100 and centered over the hole 104 in the base 100. The lens 200 may be connected to the base 100 via placing tabs 204 and into recess 112 to provide an interlocking connection between the base 100 and the lens 200.

Figure 12C:
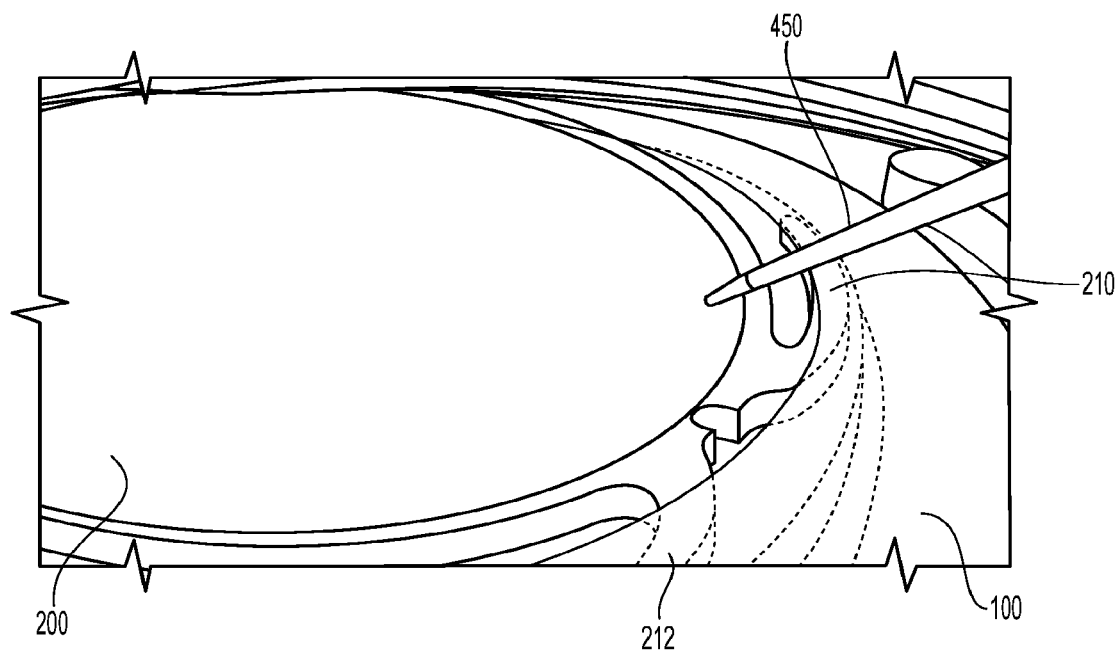
Figure 12D:
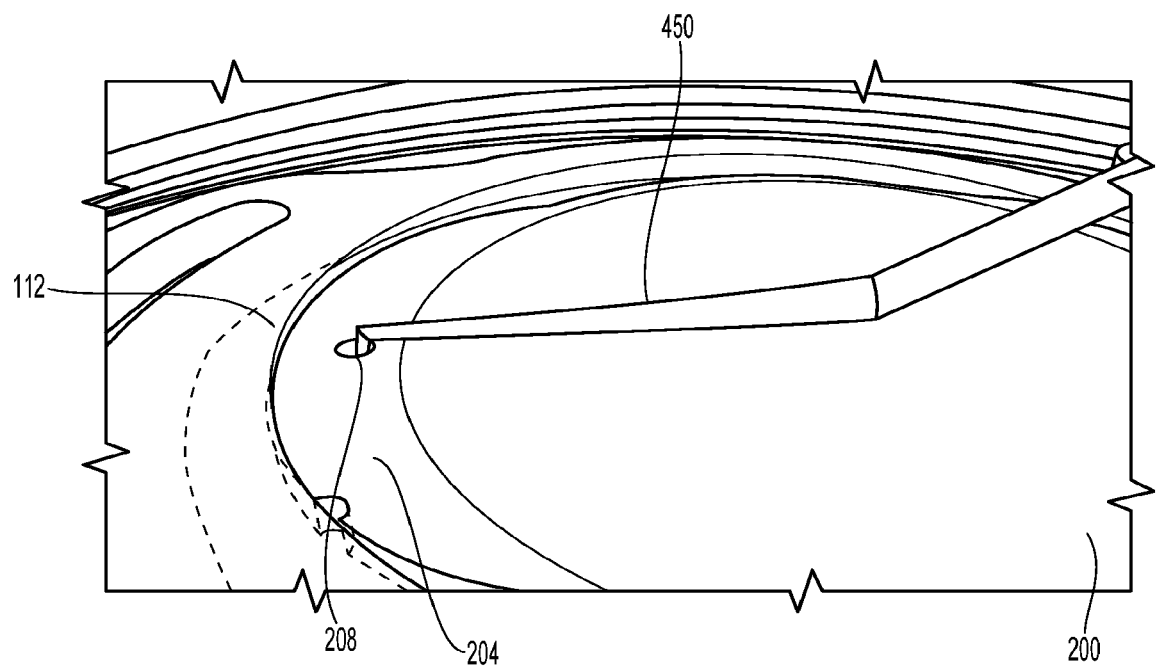

As shown in FIGS. 12C-12D, the lens 200 may be connected to the base 100 by first inserting the actuatable tab 206 into the recess 112. With respect to FIG. 12C, it should be understood that the actuatable tab may have the features of actuatable tab 206 of FIG. 3. The actuatable tab 206 may be maneuvered into the recess 112 using a probe 450. Alternatively, the actuatable tab 206 may be maneuvered into the recess 112 during the injection step using the injector 300 to steer the lens 200. In this alternative, the lens 200 is partially ejected from the injector 300 and the actuatable tab 206 is placed in the recess 112 of the base 100 while the fixed tab 204 remains in the injector 300. Once the actuatable tab 206 is in the recess 112, the lens 200 may be completely ejected from the injector 300.

The actuatable tab 206 may then be compressed by application of a lateral force using a probe 450 or similar device inserted into hole 208 of fixed tab 204, allowing the lens 200 to be advanced into the hole 104 of the base 100 such that the lens 200 and base 100 are coplanar. The compressive force may then be released from the actuatable tab 206, allowing the fixed tab 204 to slide into the recess 112 of the base 100, thus connecting the lens 200 to the base 100. Reverse steps may be followed to disconnect the lens 200 from the base 100.

Alternatively, the actuatable tab 206 may be compressed using the injector 300. In this alternative, the lens 200 is partially ejected from the injector 300 such that the actuatable tab 206 is placed in the recess 112 of the base 100 and the fixed tab 204 remains in the injector 300. Pushing the lens 200 using the injector 300 compresses the actuatable tab 206 in the recess 112. A probe may be inserted into a second corneal incision to apply a counter-force to the base 100 as the actuatable tab 206 is compressed. The lens 200 may then be positioned co-planar with the base 100 using the injector 300 such that the fixed tab 204 is aligned with the recess 112. The lens 200 may then be completely ejected from the injector 300, thus releasing the compression of the actuatable tab 206 and allowing the fixed tab 204 to move into the recess 112 of the base 100.

Prior to delivery of the lens 200, the lens 200 may be folded or rolled and placed into an injector 300 for delivery as described above. As described with reference to FIG. 3, the lens 200 may be rolled about axis 220 or axis 222, for example, which essentially bisect the lens 200. The lens 200 may be rolled in an anterior direction or a posterior direction. In one example, lens 200 may be folded or rolled from one end to the other in a manner similar to how a poster may be rolled. Alternatively, in another example, opposing ends of lens 200 may be folded rolled inward toward axis 220 or axis 222.

Lens 200 may be rolled about axis 220, to facilitate the aforementioned partial ejection of lens 200 from injector 300 (i.e., where actuatable tab 206 is outside of injector 300, while fixed tab 204 remains within injector 200). Alternatively, if the lens 200 is rolled about axis 222 in a posterior direction, then the tabs 204 and 206 may naturally move into the recess 112 of the base 100 as the lens 200 is allowed to unfurl after being positioned in the center hole 104 coplanar with the annular ring 102. This technique may negate the need to compress the actuatable tab 206 to connect the lens 200 to the base 100.

Figure 12E:
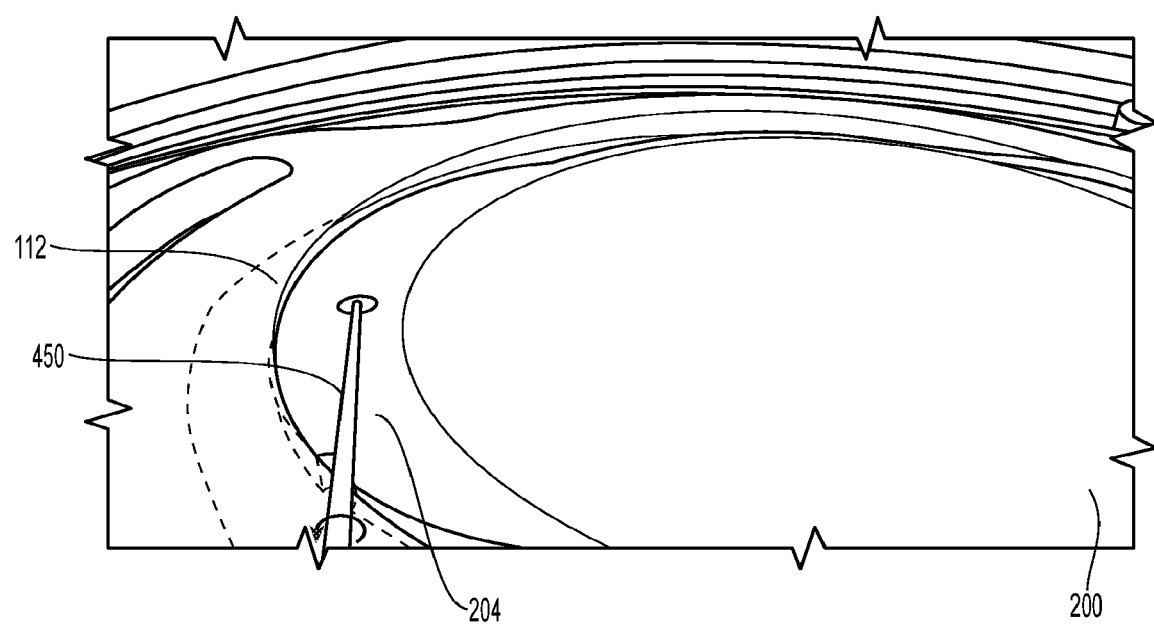

Another technique that may negate the need to compress the actuatable tab 206 to connect the lens 200 to the base 100 involves applying torque to fixed tab 204. With reference to FIG. 12E, the lens 200 is ejected from the injector 300 and positioned on the anterior side of the base 100. The actuatable tab 206 is placed in the recess 112 of the base. A probe 450 is placed in the hole 208 in the fixed tab 204. Torque is applied to the fixed tab 204 by rotating probe 450 causing the fixed tab 204 to deflect posteriorly and radially inward and the optic 202 to bow anteriorly. The fixed tab 204 is then aligned with the recess 112 in the base 100, and the torque is released, causing the fixed tab 204 to extend radially outward to its resting position in the recess 112 of the base 100.

Figure 13A:
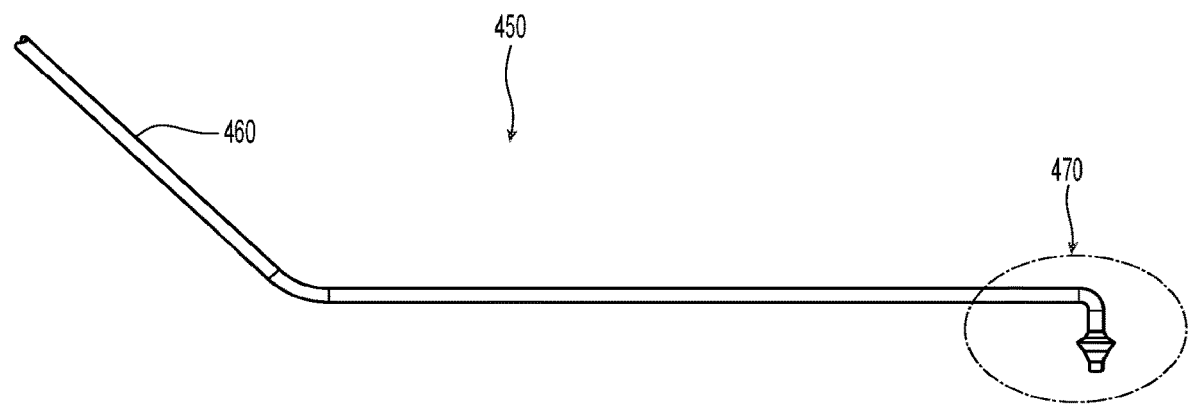
FIGS. 13A and 13B show an embodiment of a probe for use with a modular IOL according to the present disclosure.
Figure 13B:
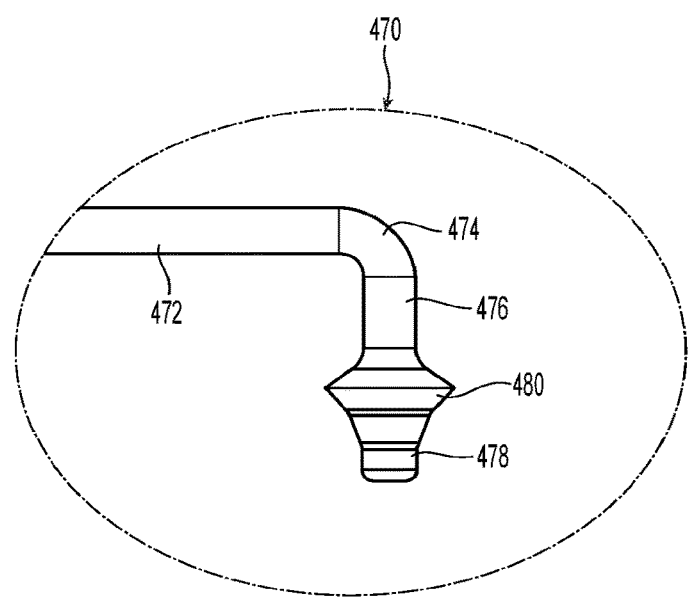

With reference to FIGS. 13A and 13B, an embodiment of a probe 450 is shown schematically. Probe 450 may be similar to a Sinskey hook commonly used in cataract surgery today, with a few variations. As shown in FIG. 13A, probe 450 includes a shaft 460 and a distal portion 470. The proximal handle portion of the probe 450 is not shown but may be a standard Sinskey handle. The distal portion shown in detail in FIG. 13B includes a distal shaft 472, an elbow 474, an elbow extension 476, an insertion tip 478 and a collar 480. Insertion tip 478 is sized to fit in hole 208 on the lens 200 for manipulation thereof. Collar 480 is sized to be larger than the hole 208 such that the tip 478 does not become deep seated in the hole 208, thereby avoiding the probe 450 becoming stuck to the lens 200.

Figure 14A:
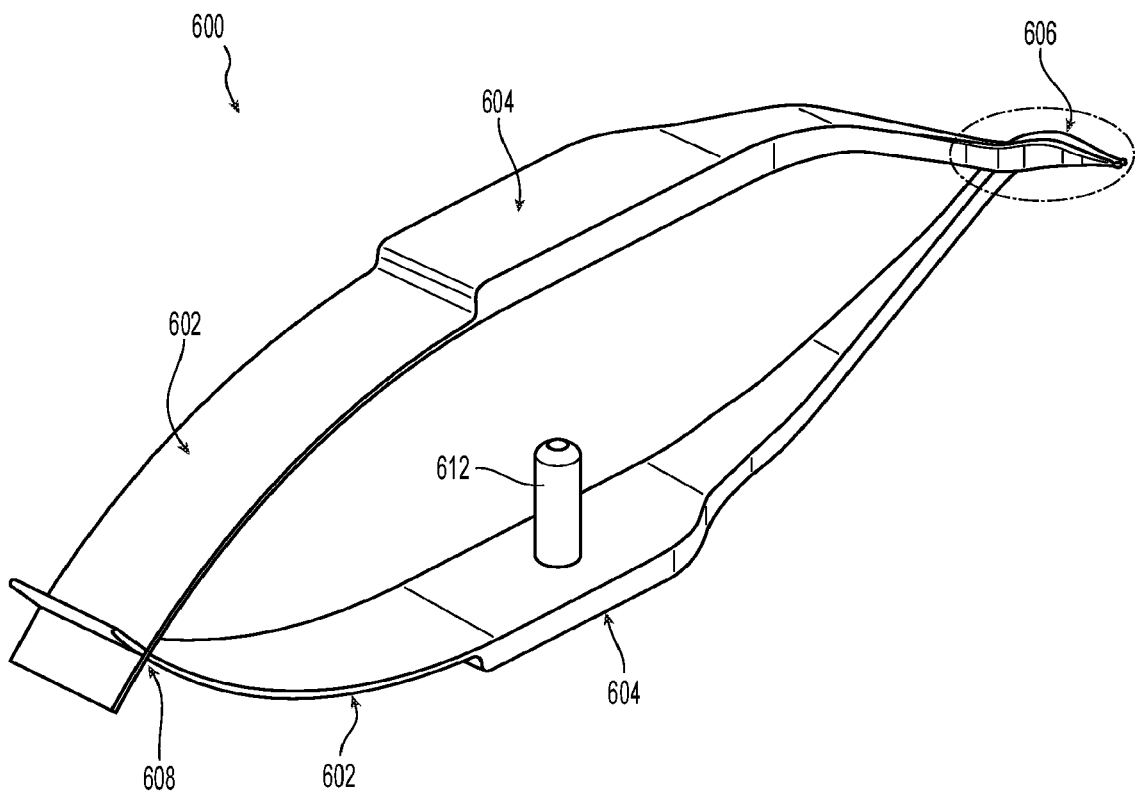
FIGS. 14A and 14B show an embodiment of forceps for use with a modular IOL according to the present disclosure.
Figure 14B:
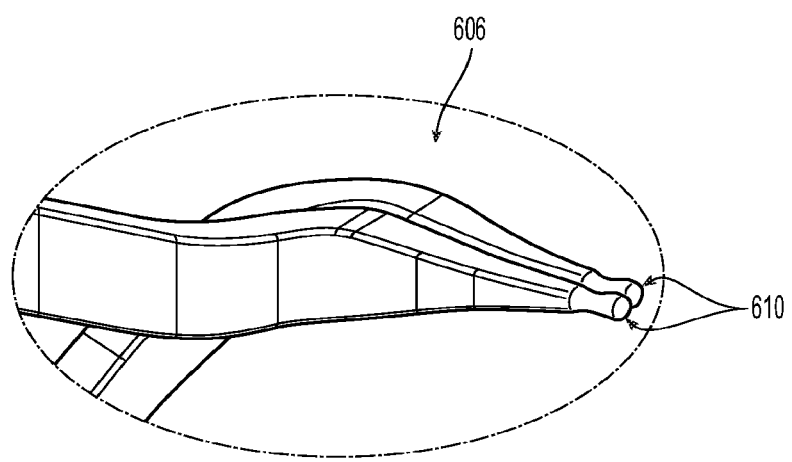

With reference to FIGS. 14A and 14B, an embodiment of folding forceps 600 is shown. Folding forceps 600 includes a pair of leaf spring arms 602, each with a grip portion 604 and an angled distal portion 606. The arms 602 are connected proximally at junction 608. The distal portion 606 includes a tip 610 associated with each of the arms. Arms 602 are biased as shown but may be squeezed to separate the distal tips 610, limited by stop 612. With this arrangement, the arms 602 may be squeezed and the tips 610 may be inserted into diametrically opposed holes or notches in the lens, such as hole 208 and notch 216 of lens 200, or holes 516 and 518 of lens 500. Upon release of the arms 602, the tips 610 move closer together causing the lens 200 or 500 to vault and the corresponding tabs 204/206 or 504/506 to move closer together. With the tabs 204/206 or 504/506 closer together, they may be inserted into the recess 112/412 of the base 100/400 without the need to compress the actuatable tab 206/506 of the lens 200/500.

The foregoing discussion of the disclosure has been presented for purposes of illustration and description. The foregoing is not intended to limit the disclosure to the form or forms disclosed herein. Although the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:
1. A modular intraocular lens (IOL) system, comprising:
a base, comprising:
an anterior section surrounding an anterior opening, wherein the anterior section has an anterior end,
a posterior section surrounding a posterior opening, wherein the posterior section has a posterior end,
a wall extending between the anterior and the posterior sections, wherein the wall includes a radially inner surface, and wherein a ratio between: (a) a dimension of the base between the anterior and the posterior ends, measured along an anterior-posterior direction, and (b) a diameter of the base, is between 0.11 and 0.14, a passage extending through the base from the anterior opening to the posterior opening, and a recess surrounding the passage, wherein the recess is defined by surfaces of:
(a) the anterior and the posterior sections, and
(b) the radially inner surface of the wall; and a lens configured for insertion into and removal from the base, the lens comprising:
an optic, and
at least one tab protruding from the optic, wherein when the lens is inserted into the base, the tab is received by the recess of the base, and the optic extends across the passage of the base.

2. The modular IOL system of claim 1, wherein the dimension of the base between the anterior and the posterior ends, measured along the anterior-posterior direction, is 1.01 mm, and wherein the diameter of the base is 7.68 mm to 7.88 mm.

3. The modular IOL system of claim 1, wherein a thickness of the anterior section decreases as the anterior section approaches the anterior opening.

4. The modular IOL system of claim 1, wherein the anterior section is sloped relative to the wall.

5. The modular IOL system of claim 1, wherein an anterior surface of the anterior section is sloped relative to the wall.

6. The modular IOL system of claim 1, wherein a posterior surface of the anterior section is sloped relative to the wall.

7. The modular IOL system of claim 1, wherein anterior and posterior surfaces of the anterior section have different slopes relative to the wall.

8. The modular IOL system of claim 1, wherein each of the anterior and the posterior surfaces of the posterior section includes a part extending perpendicular to the wall.

9. The modular IOL system of claim 1, wherein each of the anterior and the posterior surfaces of the posterior section includes a part that is sloped relative to the wall.

10. The modular IOL system of claim 1, wherein the posterior section includes a dimension, measured along the anterior-posterior direction, that is 0.15 mm.

11. The modular IOL system of claim 1, wherein:
(a) a diameter of the anterior opening is 6.40 mm;
(b) a diameter of the recess is 7.00 mm; and/or
(c) a diameter of the posterior opening is 5.30 mm.

12. The modular IOL system of claim 1, wherein the base further comprises a pair of haptics protruding radially outwardly from the wall, and wherein a distance between tips of the pair of haptics is between 12.80 mm and 13.20 mm.

13. The modular IOL system of claim 12, wherein the base has a hole extending through one of the haptics, and wherein a distance between a central longitudinal axis of the base and a central longitudinal axis of the hole is 4.25 mm.

14. The modular IOL system of claim 1, wherein:
(a) the lens has a maximum width of 6.92 mm;
(b) the optic has a diameter between 5.36 mm and 5.66 mm;
(c) the optic has a thickness, measured along the anterior-posterior direction, of 0.20 mm;
(d) the at least one tab has a thickness, measured along the anterior-posterior direction, between 0.28 mm and 0.32 mm; and/or
(e) the at least one tab has a hole extending therethrough, the hole having a diameter between 0.26 mm and 0.30 mm.

* * * * *